(12) United States Patent
Aiello et al.

(10) Patent No.: US 8,658,685 B2
(45) Date of Patent: *Feb. 25, 2014

(54) METHODS FOR TREATMENT OF KALLIKREIN-RELATED DISORDERS

(75) Inventors: Lloyd P. Aiello, Belmont, MA (US); Tamie Jo Chilcote, San Francisco, CA (US); Sukanto Sinha, San Francisco, CA (US); Edward P. Feener, North Reading, MA (US)

(73) Assignees: Activesite Pharmaceuticals, Inc., San Francisco, CA (US); Joslin Diabetes Center, Boston, MA (US)

( * ) Notice: Subject to any disclaimer, the term of this patent is extended or adjusted under 35 U.S.C. 154(b) by 326 days.

This patent is subject to a terminal disclaimer.

(21) Appl. No.: 12/865,332

(22) PCT Filed: Jan. 30, 2009

(86) PCT No.: PCT/US2009/000609
§ 371 (c)(1),
(2), (4) Date: Nov. 24, 2010

(87) PCT Pub. No.: WO2009/097141
PCT Pub. Date: Aug. 6, 2009

(65) Prior Publication Data
US 2011/0065757 A1   Mar. 17, 2011

Related U.S. Application Data

(60) Provisional application No. 61/063,107, filed on Jan. 31, 2008.

(51) Int. Cl.
*A61K 31/415* (2006.01)
*A61K 31/44* (2006.01)
*A61K 31/34* (2006.01)

(52) U.S. Cl.
USPC ........... 514/406; 514/336; 514/343; 514/469; 514/866

(58) Field of Classification Search
USPC .......................... 514/406, 336, 343, 469, 866
See application file for complete search history.

(56) References Cited

U.S. PATENT DOCUMENTS

| | | | | |
|---|---|---|---|---|
| 7,625,944 B2 * | 12/2009 | Sinha et al. | .................. | 514/469 |
| 7,997,380 B2 * | 8/2011 | Arian et al. | .................. | 181/102 |
| 8,258,170 B2 * | 9/2012 | Sinha et al. | .................. | 514/406 |
| 2001/0034023 A1 | 10/2001 | Stanton et al. | | |
| 2003/0069258 A1 | 4/2003 | Lam et al. | | |
| 2004/0209863 A1 | 10/2004 | Pinto et al. | | |
| 2006/0018896 A1 | 1/2006 | Schwaeble et al. | | |

FOREIGN PATENT DOCUMENTS

| | | |
|---|---|---|
| WO | 2006027135 A1 | 3/2006 |
| WO | 2006091459 A2 | 8/2006 |
| WO | 2008016883 A2 | 2/2008 |
| WO | 2008091692 A2 | 7/2008 |

OTHER PUBLICATIONS

Supplementary European Search Report, Issued Aug. 9, 2011, from European Patent Application No. EP 09706933.0.

* cited by examiner

*Primary Examiner* — Kevin E Weddington
(74) *Attorney, Agent, or Firm* — Pierce Atwood LLP; Kevin M. Farrell; Joseph Maraia

(57) ABSTRACT

We have identified classes of kallikrein inhibitors as compounds that are useful in the reduction of vascular permeability (e.g., retinal vascular permeability and cerebral vascular permeability) and astrocyte activation. Diseases and conditions associated with increased vascular permeability include diabetic retinopathy, hemorrhagic stroke, and macular edema. Diseases and conditions associated with astrocyte activation include Alzheimer's disease, multiple sclerosis, Parkinson's disease, amyotrophic lateral sclerosis, Creutzfeldt-Jakob disease, stroke, epilepsy, and brain trauma.

24 Claims, 15 Drawing Sheets

METHODS FOR TREATMENT OF KALLIKREIN-RELATED DISORDERS

CROSS-REFERENCE TO RELATED APPLICATIONS

This application is the National Stage of International Application No. PCT/US2009/000609, filed Jan. 30, 2009, which claims benefit of U.S. Provisional Application No. 61/063,107, filed Jan. 31, 2008, each of which is incorporated by reference herein.

STATEMENT AS TO FEDERALLY FUNDED RESEARCH

This invention was made with United States Government support under grant 1R43HL090132-01 awarded by the National Institutes of Health to ActiveSite Pharmaceuticals and under DK60165 and DK36836 by the National Institutes of Health to the Joslin Diabetes Center. The Government has certain rights to this invention.

BACKGROUND OF THE INVENTION

The invention relates to methods for treating plasma kallikrein-related disorders, such as diseases or conditions associated with increased vascular permeability or astrocyte activation. Such diseases include diabetic retinopathy, macular edema, intracerebral hemorrhage, brain edema, and stroke.

Diabetic retinopathy (DR) is a well-characterized, sight-threatening, chronic ocular disorder that eventually develops to some degree in nearly all patients with diabetes mellitus (DM; Kempen et al., *Arch. Ophthalmol.* 122:552-563 (2004) and Williams et al., *Eye* 18:963-983 (2004)). Intensive glycemic and blood pressure control is associated with a delay in onset and a slowing of the progression of diabetic retinopathy. Nevertheless, DR is the leading cause of new cases of legal blindness among Americans between the ages of 20 and 74 years. The pathological changes associated with DR are similar in both type 1 and type 2 DM, although there is a higher risk of more frequent and severe ocular complications in type 1 diabetes mellitus (DM).

Diabetic retinopathy is characterized by gradual progressive alterations in the retinal microvasculature leading to areas of retinal non-perfusion, increased vasopermeability and pathologic intraocular proliferation of retinal vessels. The complications associated with the increased vasopermeability in the macula (termed macular edema) and uncontrolled neovascularization (termed proliferative diabetic retinopathy) can result in severe and permanent visual loss. After 15-20 years of DM, nearly all patients with type 1 DM and over 60% of those with type 2 DM will have some degree of retinopathy (Aiello et al., *Diabetes Care.* 21:143-156 (1998)). DR progresses in a predictable fashion through distinctly definable stages. It is divided into two broad categories, non-proliferative diabetic retinopathy (NPDR) and proliferative diabetic retinopathy (PDR). These groups are further subdivided by level of severity. The risk of developing PDR, the most severe sight threatening form of retinopathy, increases as the level of NPDR increases (Early Treatment Diabetic Retinopathy Study Research Group, *Ophthalmol.* 98:766-785 (1991)).

Diabetic macular edema (DME) is a major cause of moderate visual loss and legal blindness in persons with type 2 diabetes (Javitt et al., *Diabetes Care.* 17:909-917 (1994)). DME can occur at any level of NPDR or PDR. Macular edema is the clinically evident accumulation of extracellular fluid in the retinal tissues of the macular area. In the United States alone, there are an estimated 500,000 people with DME and 325,000 with the more visually threatening clinically significant macular edema (CSME; Javitt et al., (1994); Javitt et al., *Ophthalmol.* 98:1565-1573 (1991); Javitt et al., *Ann. Intern. Med.* 124:164-169 (1996); Witkin et al., *JAMA.* 251:2534-2537 (1984)). An estimated 80,000 cases of DME and 56,000 cases of CSME occur each year as a result of diabetic retinopathy (Klein et al., *Ophthalmol.* 102:7-16 (1995); Javitt et al., *Ophthalmol.* 96:255-264 (1989)). The incidence of developing DME has been estimated from large epidemiological population-based surveys to be approximately 20-26% in type 1 patients (Klein et al., (1995); Klein et al., *Ophthalmol.* 105:1801-1815 (1998)), 25% in type 2 patients using insulin, and 14% in type 2 patients not requiring insulin (Klein et al., *Ophthalmol.* 102:7-16 (1995)).

Intracerebral hemorrhage (ICH) accounts for 10-15% of all cases of stroke and is associated with the highest mortality rate, with only 38% of affected patients surviving the first year (Dennis et al., *Stroke* 24:796-800 (1993)). The prognosis of ICH is poor, usually much worse than that of ischemic strokes of similar size (Pfohman et al., *J. Neurosci. Nurs.* 33:39-41 (2001)). Moreover, up to 30% of patients with ischemic stroke undergo hemorrhagic transformation (Lyden et al., *Cerebrovasc. Brain Metab. Rev.* 5:1-16 (1993)), and a number of patients with ischemic infarct after thrombolysis also develop hemorrhagic conversion (The NINDS t-PA Stroke Study Group, *Stroke* 28:2109-2118 (1997)). ICH generates neurological deterioration due to hematoma expansion and brain edema development (Brott et al., *Stroke* 28:1-5 (1997); Kazui et al., *Stroke* 28:2370-2375 (1997)). Hyperglycemia causes more profound brain edema, perihematomal cell death and a higher hemorrhagic transformation rate in experimental ICH (Song et al., *Stroke* 34:2215-2220 (2003); Demchuk et al., *Stroke* 30:34-39 (1999)). However, the precise mechanism of hematoma growth and edema formation after ICH is still unknown.

Stroke remains a leading cause of death and long-term disability in the United States. The increased risk of stroke has been linked to the pathophysiological changes seen in the cerebral vessels of individuals with diabetes (Kissela et al., *Diabetes Care* 28:355-359 (2005). In many epidemiological studies, type 2 diabetes mellitus (DM) has been an important risk factor for ischemic stroke (Almdal et al., *Arch. Intern. Med.* 164:1422-1426 (2004); however, only a few small studies have examined the risk of stroke in patients with type 1 DM during the past few decades. A recent study from the Nurses' Health Study, by investigating a very large cohort, reported that relative risks for total stroke was four-fold higher in women with type 1 DM and two-fold higher in women with type 2 DM than for non-diabetic (NDM) women. The multivariate relative risks of ischemic stroke was increased six-fold in type 1 and two-fold in type 2 DM. Moreover, type 1 DM was also significantly associated with the risk of hemorrhagic stroke (four fold), but type 2 DM was not (Janghorbani et al., *Diabetes Care* 30:1730-1735 (2007)).

Type 1 DM patients, especially those with a non-optimal metabolic control, have a higher risk of developing all microvascular complications including stroke (Kempen et al., *Arch. Ophthalmol.* 122:552-563 (2004)). Stroke is associated with decreased blood flow to the brain caused by a thrombus or rupture of a blood vessel. Moreover, thrombogenic stroke can undergo spontaneous hemorrhagic transformation, which can often be exacerbated by the combination of anticoagulation therapy. One of the outcomes of central nervous system damage caused by stroke is the breakdown of the blood-brain barrier (BBB) and increased local blood vessel permeability, which result in brain edema and neuronal and glial damage. Both clinical and experimental studies have shown that hyperglycemia has a deleterious effect on the BBB and causes edema formation after global ischemia or hemorrhage, however the mechanisms that mediate the adverse effect of diabetes and hyperglycemia on cerebral vascular function have received little attention (Williams et al., *Eye.* 18:963-983 (2004); The Diabetes Control and Complications Trial Research Group, *N. Engl. J. Med.* 329:977-986 (1993); Stratton et al., *BMJ.* 321:405-412 (2000); UK Prospective Diabetes Study Group, *BMJ.* 317:703-713 (1998)). Therapies to prevent or treat intracerebral hemorrhage remain a major unmet clinical need.

SUMMARY OF THE INVENTION

We have discovered that plasma kallikrein inhibitors, as exemplified by the compounds ASP-440 and ASP-465, are useful in decreasing vascular permeability, cerebral hemorrhage, and astrocyte activation, and the present invention therefore features methods for decreasing vascular permeability, decreasing cerebral hemorrhage, or decreasing astrocyte activation by administering such compounds to a subject. In certain embodiments, the subject has a disease associated with increased vascular permeability or a disease associated with increased astrocyte activation.

In a first aspect, the invention features a method for decreasing vascular permeability in a subject in need thereof that involves administering to the subject an effective amount of a compound having the formula I or formula II. In one embodiment, the compound has the formula (I):

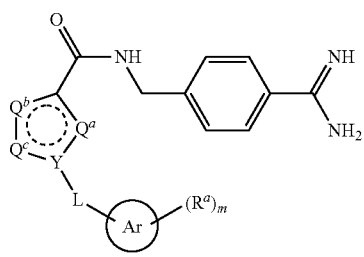

where Ar is a bond or an aromatic ring selected from the group consisting of benzene, pyridine and pyrimidine. When Ar is a bond, m is 1. When Ar is an aromatic ring, m is an integer from 0-5. In one embodiment, Ar is benzene or pyridine. In another embodiment, Ar is a bond.

The subscript m is an integer from 0 to 5. In one embodiment, m is 0.

Each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —NR$^1$—OR$^1$, —N=C=O, —N=C=S, —Si(R$^1$)$_3$, —NH—NHR$^1$, —NHC(O)NHNH$_2$, NO, —N=C=NR$^1$, and —S—CN, wherein each R$^1$ is independently alkyl, aryl, or arylalkyl. In one embodiment, R$^1$ is C$_1$-C$_8$ alkyl. In another embodiment, R$^1$ is unsubstituted aryl, such as phenyl or pyridyl, or a substituted aryl, such as a substituted phenyl or a substituted pyridyl.

In one embodiment, each $R^a$ is independently selected from the group consisting of C$_1$-C$_8$ alkyl, C$_1$-C$_8$ alkoxy, aryl, aryl(C$_1$-C$_8$ alkyl), halogen, —NH$_2$, —NH(C$_1$-C$_8$ alkyl), —N(C$_1$-C$_8$ alkyl)$_2$, —CN, —C(=O)(C$_1$-C$_8$ alkyl), —(C=O)NH$_2$, —(C=O)NH(C$_1$-C$_8$ alkyl), —C(=O)N(C$_1$-C$_8$ alkyl)$_2$, —OH, —COOH, —COO(C$_1$-C$_8$ alkyl), —OCO(C$_1$-C$_8$ alkyl), —O(C=O)O(C$_1$-C$_8$ alkyl)-NO$_2$, —SH, —S(C$_1$-C$_8$ alkyl), —NH(C=O)(C$_1$-C$_8$ alkyl), —NH(C=O)O(C$_1$-C$_8$ alkyl), —O(C=O)NH(C$_1$-C$_8$ alkyl), —SO$_2$(C$_1$-C$_8$ alkyl), —NHSO$_2$(C$_1$-C$_8$ alkyl), and —SO$_2$NH(C$_1$-C$_8$ alkyl). In another embodiment, each $R^a$ is independently selected from the group consisting of C$_1$-C$_8$ alkyl, C$_1$-C$_8$ alkoxy, phenyl, phenyl (C$_1$-C$_8$ alkyl), halogen, —CN, —NH$_2$, —NH(C$_1$-C$_8$ alkyl), —N(C$_1$-C$_8$ alkyl)$_2$, —(C=O)CH$_3$, —(C=O)NH$_2$, —OH, —COOH, —COO(C$_1$-C$_8$ alkyl), —OCO(C$_1$-C$_8$ alkyl), —O(C=O)O(C$_1$-C$_8$ alkyl), —NO$_2$, —SH, —S(C$_1$-C$_8$ alkyl), and —NH(C=O)(C$_1$-C$_8$ alkyl). In yet another embodiment, each $R^a$ is independently selected from the group consisting of C$_1$-C$_8$ alkyl, C$_1$-C$_8$ alkoxy, phenyl, phenyl (C$_1$-C$_8$ alkyl), phenoxy, aryloxy, halogen, —CN, —NH$_2$, —NH-aryl, —(C=O)CH$_3$, —(C=O)NH$_2$, —OH, —COOH, —COO(C$_1$-C$_8$ alkyl), —OCO(C$_1$-C$_8$ alkyl), —COO-aryl, —OC(O)-aryl, —O(C=O)O(C$_1$-C$_8$ alkyl)-NO$_2$, —SH, —S(C$_1$-C$_8$ alkyl), —NH(C=O)(C$_1$-C$_8$ alkyl), and the like. For example, $R^a$ is halogen, such as Cl, Br or I.

L is a linking group selected from the group consisting of a bond, CH$_2$, and SO$_2$.

$Q^a$, $Q^b$, and $Q^c$ are each members independently selected from the group consisting of N, S, O, and C(R$^q$) wherein each R$^q$ is independently selected from the group consisting of H, C$_{1-8}$ alkyl, halogen, and phenyl, and the ring having $Q^a$, $Q^b$, $Q^c$, and Y as ring vertices is a five-membered ring having two double bonds.

In a first group of embodiments, $Q^a$ is N and $Q^b$ and $Q^c$ are each selected from N, O, and C(R$^q$). In certain instances, $Q^a$ is N and $Q^c$ and $Q^b$ are each independently selected from N and C(R$^q$). In certain other instances, $Q^a$ is N and $Q^c$ and $Q^b$ are each selected from C(R$^q$) and O. In yet certain other instances, $Q^a$ is N, $Q^c$ is a member selected from N and O, and $Q^b$ is the other member selected from N and O.

In a second group of embodiments, $Q^a$ is O and $Q^b$ and $Q^c$ are each selected from N, O, and C(R$^q$). In certain instances, $Q^a$ is O and $Q^c$ and $Q^b$ are each independently selected from N and C(R$^q$).

In a third group of embodiments, $Q^a$ is C(R$^q$) and $Q^b$ and $Q^c$ are each selected from N, O, and C(R$^q$). In certain instances, $Q^a$ is C(R$^q$) and $Q^b$ and $Q^c$ are each independently selected from N and O. In certain other instances, $Q^a$ is C(R$^q$) and $Q^b$ and $Q^c$ are each independently selected from N and C(R$^q$). In yet certain other instances, $Q^a$ is C(R$^q$) and $Q^b$ and $Q^c$ are each independently selected from O and C(R$^q$). In one occurrence, $Q^a$ is C(R$^q$), $Q^b$ is O and $Q^c$ is (CR$^q$).

Y is a member selected from the group consisting of C and N. In one embodiment, Y is C, $Q^a$ is S and Ar is selected from phenyl or pyridyl. In another embodiment, Y is N, $Q^a$, $Q^b$, or $Q^c$ are each independently C(R$^q$), wherein R$^q$ is H or C$_{1-8}$ alkyl. In one instance, Y is N, $Q^a$ and $Q^c$ are C(R$^q$) and $Q^b$ is CH. In a preferred embodiment, Y is N.

In one embodiment, L is a bond, Y is N. In another embodiment, L is a bond, Y is N and Ar is a benzene ring. In yet another embodiment, L is CH₂ and Y is N. In still another embodiment, L is a bond and Y is C. In a further embodiment, L is SO₂ and Y is N.

In a preferred embodiment $Q^a$, $Q^b$, and $Q^c$ are each independently $CR^a$. In another preferred embodiment, L is a bond or CH₂. In still another preferred embodiment, Ar is benzene. In still another preferred embodiment, $R^a$ is —H and $C_1$-$C_8$ alkyl.

Particular compounds of formula I are set forth in Table 1 below:

TABLE 1

ASP-465

ASP-440

ASP-466

ASP-445

ASP-558

TABLE 1-continued

ASP-523

ASP-559

ASP-373

ASP-525

ASP-576

ASP-577

ASP-578

TABLE 1-continued

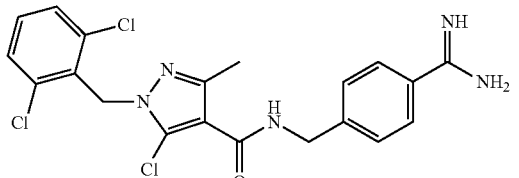
ASP-579

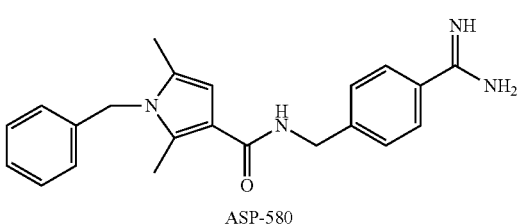 [SMILES: Cc1cc(C(=O)NCc2ccc(C(=N)N)cc2)c(C)n1Cc1ccccc1]
ASP-580

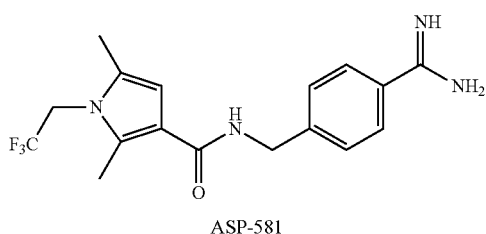 [SMILES: Cc1cc(C(=O)NCc2ccc(C(=N)N)cc2)c(C)n1CC(F)(F)F]
ASP-581

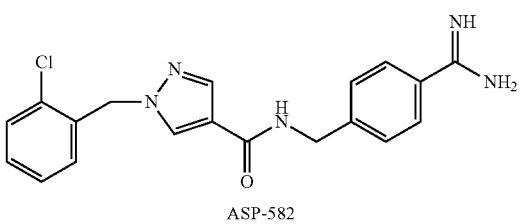 [SMILES: N=C(N)c1ccc(CNC(=O)c2cnn(Cc3ccccc3Cl)c2)cc1]
ASP-582

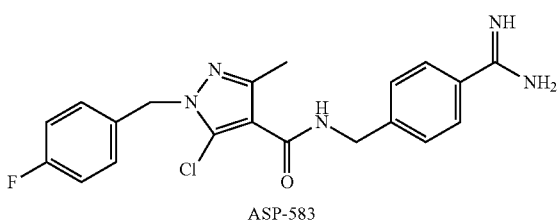 [SMILES: Cc1nn(Cc2ccc(F)cc2)c(Cl)c1C(=O)NCc1ccc(C(=N)N)cc1]
ASP-583

In another embodiment, the compound of formula I has a subformula Ia:

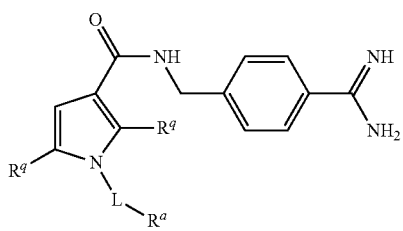

$R^q$ and L are as defined above. In one instance, $R^q$ is independently —H or $C_{1-8}$ alkyl and L is a bond or —CH$_2$—. In another instance, $R^q$ is halo-($C_1$-$C_8$ alkyl). For example, $R^q$ is —CF$_3$, CH$_2$CF$_3$.

In one embodiment, the compounds of formula I have a subformula Ib:

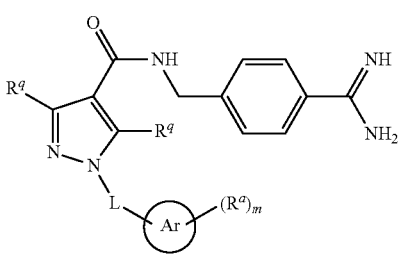
Ib wherein Ar is an aromatic ring. In one instance, each $R^q$ is independently H, $C_1$-$C_8$ alkyl, or halogen. In another instance, L is a bond or CH$_2$. In yet another instance, Ar is benzene. In still another instance, m is 0. In one occurrence, each $R^q$ is H, L is CH$_2$, Ar is benzene, and m is 0. In another occurrence, each $R^q$ is H, L is a bond, Ar is benzene, and m is 0.

In another aspect, the present invention includes the use of a compound having the formula II:

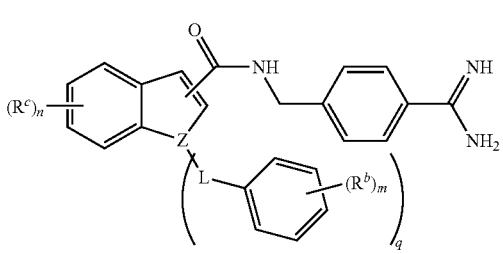
II

The subscript m is an integer of from 0 to 5. The subscript n is an integer of from 0 to 4. The subscript q is an integer of from 0 to 1. In one embodiment, the subscript m is 0. In another embodiment, the subscript n is an integer from 0 to 2. In yet another embodiment, the subscript q is 0. In still another embodiment, the subscript q is 1.

L is a linking group selected from the group consisting of a bond, CH$_2$ and SO$_2$. In one embodiment, L is CH$_2$ or SO$_2$.

Each of $R^b$ and $R^c$ is independently selected from the group consisting of cycloalkyl, haloalkyl, halogen, —OH, —OR$^2$, —OSi(R$^2$)$_3$, —OC(O)O—R$^2$, —OC(O)R$^2$, —OC(O)NHR$^2$, —OC(O)N(R$^2$)$_2$, —SH, —SR$^2$, —S(O)R$^2$, —S(O)$_2$R$^2$, —SO$_2$NH$_2$, —S(O)$_2$NHR$^2$, —S(O)$_2$N(R$^2$)$_2$, —NHS(O)$_2$R$^2$, —NR$^2$S(O)$_2$R$^2$, —C(O)NH$_2$, —C(O)NHR$^2$, —C(O)N(R$^2$)$_2$, —C(O)R$^2$, —C(O)H, —C(=S)R$^2$, —NHC(O)R$^2$, —NR$^2$C(O)R$^2$, —NHC(O)NH$_2$, —NR$^2$C(O)NH$_2$, —NR$^2$C(O)NHR$^2$, —NHC(O)NHR$^2$, —NR$^2$C(O)N(R$^2$)$_2$, —NHC(O)N(R$^2$)$_2$, —CO$_2$H, —CO$_2$R$^2$, —NHCO$_2$R$^2$, —NR$^2$CO$_2$R$^2$, —R$^2$, —CN, —NO$_2$, —NH$_2$, —NHR$^2$, —N(R$^2$)$_2$, —NR$^2$S(O)NH$_2$, —NR$^2$S(O)$_2$NHR$^2$, —NH$_2$C(=NR$^2$)NH$_2$, —N=C(NH$_2$)NH$_2$, —C(=NR$^2$)NH$_2$, —NH—OH, —NR$^2$—OH, —NR$^2$—OR$^2$, —N=C=O, —N=C=S, —Si(R$^2$)$_3$, —NH—NHR$^2$, —NHC(O)NHNH$_2$, NO, —N=C=NR$^2$, and —S—CN, wherein each R$^2$ is independently alkyl, aryl, or arylalkyl. In one embodiment, R$^2$ is $C_1$-$C_8$ alkyl. In another embodiment, R$^2$ is unsubstituted aryl, such as phenyl or pyridyl, or a substituted aryl, such as a substituted phenyl or a substituted pyridyl.

In one embodiment, each of $R^b$ and $R^c$ is independently selected from the group consisting of $C_1$-$C_8$ alkyl, $C_1$-$C_8$ alkoxy, aryl, aryl($C_1$-$C_8$ alkyl), halogen, —NH$_2$, —NH($C_1$-$C_8$ alkyl), —N($C_1$-$C_8$ alkyl)$_2$, —CN, —C(=O)($C_1$-$C_8$ alkyl), —(C=O)NH$_2$, —(C=O)NH($C_1$-$C_8$ alkyl), —C(=O)N($C_1$-$C_8$ alkyl)$_2$, —OH, —COOH, —COO($C_1$-$C_8$ alkyl), —OCO($C_1$-$C_8$ alkyl), —O(C=O)O($C_1$-$C_8$ alkyl)-NO$_2$, —SH, —S($C_1$-$C_8$ alkyl), —NH(C=O)($C_1$-$C_8$ alkyl), —NH(C=O)O($C_1$-$C_8$ alkyl), —O(C=O)NH($C_1$-$C_8$ alkyl), —$SO_2$($C_1$-$C_8$ alkyl), —$NHSO_2$($C_1$-$C_8$ alkyl), and —$SO_2$NH($C_1$-$C_8$ alkyl). In another embodiment, each $R^a$ is independently selected from the group consisting of $C_1$-$C_8$ alkyl, $C_1$-$C_8$ alkoxy, phenyl, phenyl($C_1$-$C_8$ alkyl), halogen, —CN, —$NH_2$, —NH($C_1$-$C_8$ alkyl), —N($C_1$-$C_8$ alkyl)$_2$, —(C=O)$CH_3$, —(C=O)$NH_2$, —OH, —COOH, —COO($C_1$-$C_8$ alkyl), —OCO($C_1$-$C_8$ alkyl), —O(C=O)O($C_1$-$C_8$ alkyl), —$NO_2$, —SH, —S($C_1$-$C_8$ alkyl), and —NH(C=O)($C_1$-$C_8$ alkyl). In yet another embodiment, each $R^a$ is independently selected from the group consisting of $C_1$-$C_8$ alkyl, $C_1$-$C_8$ alkoxy, phenyl, phenyl($C_1$-$C_8$ alkyl), phenoxy, aryloxy, halogen, —CN, —$NH_2$, —NH-aryl, —(C=O)$CH_3$, —(C=O)$NH_2$, —OH, —COOH, —COO($C_1$-$C_8$ alkyl), —OCO($C_1$-$C_8$ alkyl), —COO-aryl, —OC(O)-aryl, —O(C=O)O($C_1$-$C_8$ alkyl)-$NO_2$, —SH, —S($C_1$-$C_8$ alkyl), —NH(C=O)($C_1$-$C_8$ alkyl), and the like.

When q is 0, Z is a member selected from the group consisting of O, S, and $NR^d$ wherein $R^d$ is H or $C_1$-$C_8$ alkyl. When q is 1, Z is N. In one embodiment, the subscript q is 0, and Z is selected from the group consisting of O, S, and NH. In one instance, the subscript n is 0, 1 or 2. in one occurrence, Z is O or S. In another embodiment, the subscript q is 1. In one instance, L is $CH_2$ or $SO_2$.

Particular compounds of formula II are set forth in Table 2 below:

TABLE 2

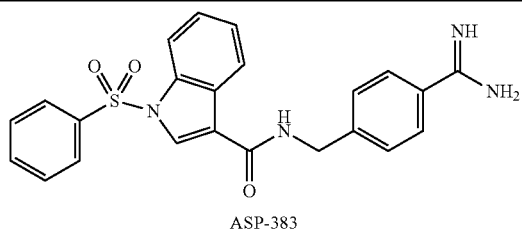

ASP-383

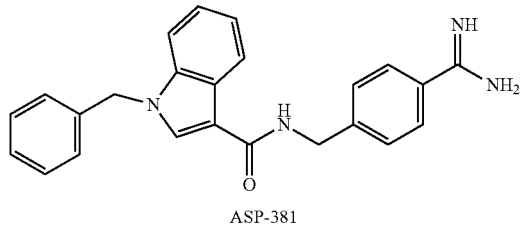 [SMILES: N=C(N)c1ccc(CNC(=O)c2cn(Cc3ccccc3)c3ccccc23)cc1]

ASP-381

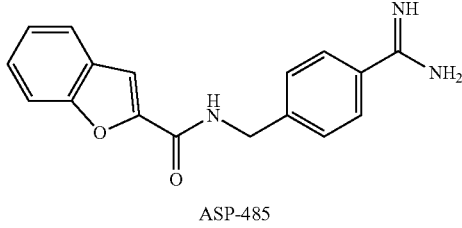 [SMILES: N=C(N)c1ccc(CNC(=O)c2cc3ccccc3s2)cc1]

ASP-485

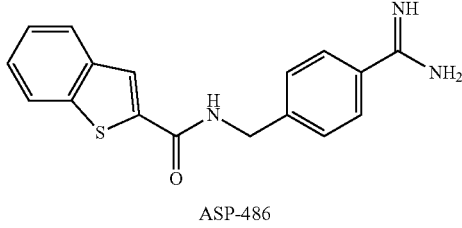

ASP-486

TABLE 2-continued

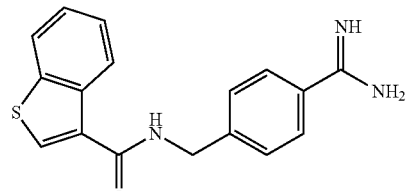

ASP-491

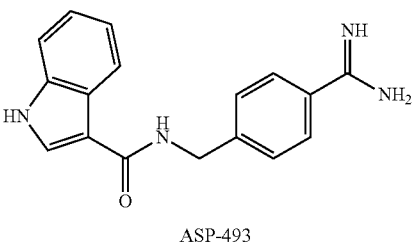 [SMILES: N=C(N)c1ccc(CNC(=O)c2c[nH]c3ccccc23)cc1]

ASP-493

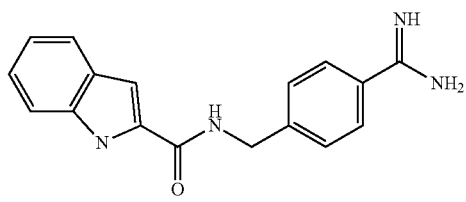

ASP-484

In one embodiment, the compound of formula I has a subformula IIa:

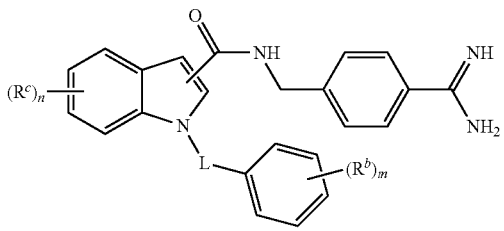

IIa

Substituents $R^b$ and $R^c$ and subscripts m are as defined above. In one instance, L is $CH_2$. In another instance, L is $SO_2$. In yet another instance, m is 0. In still another instance, n is 0.

In another embodiment, compounds of formula I have a subformula IIa-1:

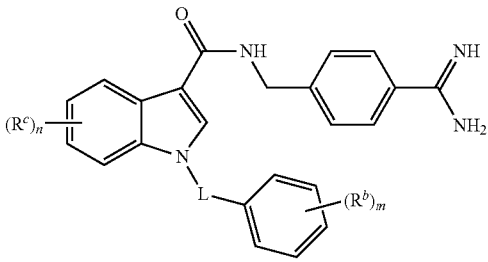

IIa-1

Table 3 provides compounds of PK inhibitors and their inhibition activities. The compound numbers correspond to numbers in Tables 1 and 2.

TABLE 3

| ASP- | Name | Calc MW | Exper. Mass (m + 1) | PK $K_{iapp}$ (μM) |
|---|---|---|---|---|
| 465 | 2,5-Dimethyl-1-pyridin-4-ylmethyl-1H-pyrrole-3-carboxylic acid 4-carbamimidoyl-benzylamide | 361.5 | 362.20 | 0.08 |
| 383 | 1-Benzenesulfonyl-1H-indole-3-carboxylic acid 4-carbamimidoyl-benzylamide | 432.5 | 433.10 | 0.17 |
| 381 | 1-Benzyl-1H-indole-3-carboxylic acid 4-carbamimidoyl-benzylamide | 382.5 | 383.20 | 0.24 |
| 440 | 1-Benzyl-1H-pyrazole-4-carboxylic acid 4-carbamimidoyl-benzylamide | 333.4 | 334.20 | 0.31 |
| 485 | Benzofuran-2-carboxylic acid 4-carbamimidoyl-benzylamide | 293.3 | | 0.87 |
| 466 | 2-Methyl-5-phenyl-furan-3-carboxylic acid 4-carbamimidoyl-benzylamide | 333.4 | 334.10 | 1.29 |
| 445 | 1-Phenyl-1H-pyrazole-4-carboxylic acid 4-carbamimidoyl-benzylamide | 319.4 | 320.10 | 1.43 |
| 486 | Benzo[b]thiophene-2-carboxylic acid 4-carbamimidoyl-benzylamide | 309.4 | | 1.57 |
| 491 | Benzo[b]thiophene-3-carboxylic acid 4-carbamimidoyl-benzylamide | 309.4 | | 2.11 |
| 493 | 1H-Indole-3-carboxylic acid 4-carbamimidoyl-benzylamide | 292.3 | | 2.45 |
| 484 | 1H-Indole-2-carboxylic acid 4-carbamimidoyl-benzylamide | 292.3 | | 2.52 |
| 558 | 1-(4-Bromo-benzyl)-5-methyl-1H-1,2,3-triazole-4-carboxylic acid 4-carbamimidoyl-benzylamide | 427.3 | 428.10 | 2.62 |
| 523 | 5-Phenyl-thiophene-2-carboxylic acid 4-carbamimidoyl-benzylamide | 335.4 | 336.10 | 7.66 |
| 559 | 1-(4-Fluoro-benzyl)-1H-1,2,3-triazole-4-carboxylic acid 4-carbamimidoyl-benzylamide | 352.4 | | 8.09 |
| 373 | 4-Methyl-2-phenyl-thiazole-5-carboxylic acid 4-carbamimidoyl-benzylamide | 350.4 | 351.10 | 8.87 |
| 525 | 5-Pyridin-2-yl-thiophene-2-carboxylic acid 4-carbamimidoyl-benzylamide | 336.4 | | 20.57 |
| 576 | 2,5-Dimethyl-1-phenyl-1H-pyrrole-3-carboxylic acid 4-carbamimidoyl-benzylamide | 346.4 | 347.1 | 0.04 |
| 577 | 1-Benzyl-3,5-dimethyl-1H-pyrazole-4-carboxylic acid 4-carbamimidoyl-benzylamide | 361.5 | 362.1 | 1.13 |
| 578 | 1-(2-Chloro-benzyl)-3,5-dimethyl-1H-pyrazole-4-carboxylic acid 4-carbamimidoyl-benzylamide | 395.9 | 396.1 | 1.64 |
| 579 | 5-Chloro-1-(2,6-dichloro-benzyl)-3-methyl-1H-pyrazole-4-carboxylic acid 4-carbamimidoyl-benzylamide | 450.8 | 450.0 | 1.19 |
| 580 | 1-Benzyl-2,5-dimethyl-1H-pyrrole-3-carboxylic acid 4-carbamimidoyl-benzylamide | 360.5 | 361.1 | 0.03 |
| 581 | 2,5-Dimethyl-1-(2,2,2-trifluoro-ethyl)-1H-pyrrole-3-carboxylic acid 4-carbamimidoyl-benzylamide | 352.4 | 353.1 | 0.41 |
| 582 | 1-(2-Chloro-benzyl)-1H-pyrazole-4-carboxylic acid 4-carbamimidoyl-benzylamide | 367.8 | 368.0 | 0.47 |
| 583 | 5-Chloro-1-(4-fluoro-benzyl)-3-methyl-1H-pyrazole-4-carboxylic acid 4-carbamimidoyl-benzylamide | 399.9 | 400.0 | 2.38 |

In the above aspect of the invention, the subject may have increased vascular permeability (e.g., increased retinal vascular permeability). In another embodiment, the subject may have, or be at increased risk of developing, a disease or condition selected from the group consisting of macular edema, non-proliferative retinopathy, proliferative retinopathy, retinal edema, complications related to cataract surgery in diabetic retinopathy, hypertensive retinopathy, retinal trauma, microalbuminuria, albuminuria, and proteinuria, or any disease or condition described herein. The subject may have or be at risk of developing type 1 or type 2 diabetes mellitus. The subject may have suffered from, or may be at increased risk of having, a hemorrhagic stroke (e.g., cerebral stroke or a subarachnoid stroke), an intracerebral hemorrhage, a hemorrhagic transformation of ischemic stroke, a cerebral trauma associated with injury or surgery, a brain aneurysm, a high altitude edema, or arterial-venous malformation. The subject may have suffered from an intracerebral hemorrhage following treatment with a fibrolytic or thrombolytic agent, such as t-PA, alteplase, Activase, reteplase, tenecteplase, streptokinase, or urokinase.

In another aspect, the invention features a method for decreasing astrocyte activation in a subject in need thereof. The method includes administering to the subject an effective amount of any of the compounds of formula I or formula II described herein (e.g., those described in the previous aspect of the invention). The subject may have a disease or condition associated with increased astrocyte activation. The disease or condition may be selected from the group consisting of Alzheimer's disease, multiple sclerosis, Parkinson's disease, amyotrophic lateral sclerosis, Creutzfeldt-Jakob disease, stroke, epilepsy, brain trauma, and any astrocyte activation disorder described herein.

The invention also features a method of treating a subject having, or at increased risk of developing, or prevent an intracerebral hemorrhage, hemorrhagic transformation of ischemic stroke, hemorrhagic stroke (e.g., a cerebral or subarachnoid hemorrhage), spread of hematoma (e.g., following stroke), cerebral trauma associated by injury or surgery, brain aneurysm, high altitude edema, arterial-venous malformation, retinopathy, diabetic retinopathy (e.g., proliferative or non-proliferative diabetic retinopathy), macular edema (e.g., diabetic macular edema (DME), clinically significant macular edema (CSME), or cystoid macular edema (CME)), complications related to cataract surgery in diabetic retinopathy, hypertensive retinopathy, or retinal trauma by administering to the subject a compound of formula I or formula II (e.g., any compound described herein) in an effective amount. The invention also features a method of treating a subject having, or at risk of developing, or preventing DME or CSME following laser panretinal (scatter) photocoagulation, post-surgical ME, (e.g., CME following cataract extraction), CME induced by cryotherapy, CME following vascular occlusion (e.g., central retina vein occlusion, branch retinal vein occlusion, or hemiretinal vein occlusion), and CME induced by uveitis by administering to the subject a compound of formula I or formula II (e.g., any compound described herein) in an effective amount. The invention further features a method of treating a subject having, or at increased risk of developing, vision loss caused by any of the conditions listed herein, including age-related macular degeneration (AMD), by administering to the subject a compound of formula I or formula II (e.g., any compound described herein) in an effective amount. The invention also features a method of treating a subject having, or at increased risk of developing, vitreous or retinal hemorrhages secondary to diabetes or retinal vascular occlusions and retinal detachment caused by proliferative diabetic retinopathy (PDR) by administering to the subject a compound of formula I or formula II (e.g., any compound described herein) in an effective amount. The invention further features a method of treating a subject having, or at increased risk of developing, Alzheimer's disease, multiple sclerosis, Parkinson's disease, amyotrophic lateral sclerosis, Creutzfeldt-Jakob disease), stroke, epilepsy, and brain trauma by administering to the subject a compound of formula I or formula II (e.g., any compound described herein) in an effective amount.

In any of the above aspects the subject may have, or may be at risk of developing diabetes (e.g., type I or type II diabetes mellitus). In other embodiments, the subject may have, or be at risk of developing, hypertension, insulin resistance, ketoacidosis, trauma, infection, or hyperglycemia. In certain embodiments, the subject may taking an additional medication (e.g., angiotensin converting enzyme (ACE) inhibitors, factors that reduce dipeptidyl peptidase IV activity, and thiazolidinediones).

In particular embodiments of any of the above aspects of the invention, the subject may not be in need of blood coagulation inhibition, or may not be suffering or may not have suffered from one or more of the following: ischemic stroke, stroke, inflammation, pain, acute myocardial infarction (MI), thrombosis (e.g., deep vein thrombosis (DVT)), coagulations from post fibrinolytic treatment conditions (e.g., treatment with tissue plasminogen activator or streptokinase), angina, angioedema, sepsis, arthritis, blood loss during cardiopulmonary bypass, inflammatory bowel disease, diabetes, diabetic complication, and retinopathy.

In any of the above aspects of the invention, the compound of formula I or formula II may be selected from the group consisting of ASP-465, ASP-440, ASP-466, ASP-445, ASP-558, ASP-523, ASP-559, ASP-373, ASP-525, ASP-576, ASP-577, ASP-578, ASP-579, ASP-580, ASP-581, ASP-582, ASP-583, ASP-383, ASP-381, ASP-485, ASP-486, ASP-491, ASP-493, and ASP-484.

In any of the above aspects of the invention, the compound of formula I or formula II may be capable of decreasing or inhibiting kallikrein activity. In some embodiments, administration of the compound to the subject treats the disease associated with increased vascular permeability or astrocyte activation, but does not reduce the blood pressure in said subject.

In any of the above aspects, the compound of formula I or formula II may be administered orally, parenterally (e.g., intravenously, intramuscularly, subcutaneously), ocularly, rectally, cutaneously, nasally, vaginally, by inhalation, or intracranially.

Disorders that may be treated using the methods of the invention include those associated with increased or excessive vascular permeability such as disorders associated with increased retinal or cerebral vascular permeability or vasogenic edema. In any of the above aspects, the method may include a step of selecting a subject on the basis that the subject has, or is at risk for developing, a disorder associated with excessive vascular permeability.

Disorders associated with excessive vascular permeability or edema in the brain include cerebral edema (e.g., high altitude edema), intracerebral hemorrhage, subdural hemorrhage, hemorrhagic stroke (e.g., cerebral or subarachnoid), and hemorrhagic transformation of ischemic stroke. Cerebral edema is an increase in brain volume caused by an absolute increase in cerebral tissue fluid content; vasogenic cerebral edema arises from transvascular leakage caused by mechanical failure of the endothelial tight junctions of the blood-brain barrier (BBB). Other diseases include brain aneurysm and arterial-venous malformation.

Disorders associated with excessive vascular permeability and/or edema in the eye, e.g., in the retina or vitreous, include age-related macular degeneration (AMID), retinal edema, retinal hemorrhage, vitreous hemorrhage, macular edema (ME), diabetic macular edema (DME), proliferative diabetic retinopathy (PDR) and non-proliferative diabetic retinopathy (DR); radiation retinopathy; telangiectasis; central serous retinopathy; retinal vein occlusions (e.g., branch or central vein occlusions), radiation retinopathy, sickle cell retinopathy, retinopathy of prematurity, Von Hipple Lindau disease, posterior uveitis, chronic retinal detachment, Irvine Gass Syndrome, Eals disease, retinitis, and choroiditis.

Other disorders associated with increased permeability include excessive vascular permeability associated with hypertension or inflammation; increased systemic vascular permeability, e.g., associated with septic shock, scurvy, anaphylaxis, hereditary or acquired angioedema (both of which have been linked to C1 inhibitor deficiency), brain aneurysm, and arterial-venous malformation. In some embodiments, the disorders associated with vascular permeability that are treated by a method described herein exclude hereditary or acquired angioedema.

In some embodiments, the disorder associated with increased permeability is also associated with hemorrhage, i.e., bleeding into the affected area. In some embodiments, the disorder associated with increased permeability is also associated with lysis of erythrocytes in the affected area.

In some embodiments, the disorder associated with increased permeability is also associated with an increased volume of fluid in the tissue, e.g., edema, and the methods described herein result in a reduction in the volume of fluid. Generally, the fluid is extracellular. Thus, included herein are methods for reducing the fluid volume in a tissue.

As used herein, by "subject" is meant either a human or non-human animal (e.g., a mammal).

By "vascular permeability" is meant the passage of substances, including molecules, particles, and cells, across the vascular endothelium. Increases in the rate or amount of such passage (i.e., increased vascular permeability) can be indicative of the disease states described herein.

"Treating" a disease or condition in a subject or "treating" a subject having a disease or condition refers to subjecting the individual to a pharmaceutical treatment, e.g., the administration of a drug, such that at least one symptom of the disease or condition is decreased or stabilized.

By "preventing" a disease or condition using a pharmaceutical treatment is meant to reduce the likelihood of occurrence or the severity of a disease or condition in a subject prior to the appearance of a symptoms of the disease or condition. In one example, a compound is administered to a subject with an increased risk of developing a disease.

By "an effective amount" is meant the amount of a compound, alone or in combination with another therapeutic regimen, required to treat a patient with a disease or condition in a clinically relevant manner. A sufficient amount of an active compound used to practice the present invention for therapeutic treatment of conditions varies depending upon the manner of administration, the age, body weight, and general health of the patient. Ultimately, the prescribers will decide the appropriate amount and dosage regimen.

By "increase" is meant a positive change of at least 5%, 10%, 25%, 50%, 100%, 250%, 500%, 1000%, 5000%, 10,000%, or 100,000% as compared to a baseline or control.

By "decrease" is meant a reduction of at least 1%, 2%, 3%, 5%, 10%, 15%, 20%, 25%, 30%, 40%, 50%, 60%, 70%, 80%, 85%, 90%, 95%, 96%, 97%, 98%, 99%, 99.5%, or 99.9% as compared to a baseline or control.

By "control" in the context of the present invention, is meant a state or value associated with a healthy (e.g., not suffering from one of the conditions or diseases described herein) subject or subjects for the relevant biological or physiological indication being compared.

By "fibrinolytic agent" is meant an drug or compound that is capable of dissolving a fibrin clot or cleaving fibrin. Fibrinolytic agents are also known as "thrombolytics." Fibrinolytic agents include, but are not limited to, t-PA (e.g., alteplase, Activase), reteplase, tenecteplase, streptokinase, and urokinase.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms.

The term "alkylene" by itself or as part of another substituent means a divalent radical derived from an alkane, as exemplified by $-CH_2CH_2CH_2CH_2-$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The term "cycloalkyl" refers to hydrocarbon rings having the indicated number of ring atoms (e.g., $C_{3-6}$ cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2]octane, etc. When a prefix is not included to indicate the number of ring carbon atoms in a cycloalkyl, the radical or portion thereof will have 8 or fewer ring carbon atoms.

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as $-NR^aR^b$ is meant to include piperidinyl, pyrrolidinyl, morpholinyl, azetidinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means a monovalent monocyclic, bicyclic, or polycyclic aromatic hydrocarbon radical of 5 to 14 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl cut, phenyl or phenylalkyl, aryl or arylalkyl), $-(CR'R'')_n-COOR$ (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl), or $-(CR'R'')_n-CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one to five heteroatoms or heteroatom functional groups have replaced a ring carbon, while retaining aromatic properties, e.g., pyridyl, quinolinyl, quinazolinyl, thienyl, and the like. The heteroatoms are selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl, and the like. For brevity, the term aryl, when used in combination with other radicals (e.g., aryloxy, arylalkyl) is meant to include both aryl groups and heteroaryl groups as described above.

Substituents for the aryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R", and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$—, or a single bond, and q is an integer from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen and unsubstituted C$_{1-6}$ alkyl.

As used herein, the term "heteroatom" is meant to include oxygen (O), nitrogen (N), sulfur (S), and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines, and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *J. Pharm. Sci.* 66:1-19, 1977). Certain specific compounds of the present invention contain both basic and acidic functionalities that allow the compounds to be converted into either base or acid addition salts. The term "pharmaceutically acceptable" is meant the carrier, diluent or excipient must be compatible with the other ingredients of the formulation and not deleterious to the recipient thereof.

Other features and advantages of the invention will be apparent from the following Detailed Description, the drawings, and the claims.

BRIEF DESCRIPTION OF THE DRAWINGS

FIG. 11C shows the effect of systemic treatment with Icatabant (Hoe 140) on blood-induced hematoma response.

DETAILED DESCRIPTION

We have identified classes of kallikrein inhibitors, as exemplified by the compounds ASP-440 and ASP-465, as being useful for reducing vascular permeability and astrocyte activation. Accordingly, compounds described by formula I or formula II can be used in the treatment of diseases or conditions associated with increased vascular permeability such as intracerebral hemorrhage, hemorrhagic stroke, hemorrhagic transformation of ischemic stroke, cerebral trauma associated by injury or surgery, cerebral edema or hematoma, high altitude edema, and arterial-venous malformation, disorders of the eye, for example, disorders related to retina vascular permeability such as diabetic macular edema, and diabetic retinopathy (e.g., nonproliferative or proliferative), complications related to cataract surgery in diabetic retinopathy, hypertensive retinopathy, and retinal trauma, or astrocyte abnormalities associated with diabetic retinopathy. In other embodiments, these compounds can also be used to treat diseases or conditions associated with astrocyte activation, which include neurodegenerative diseases (e.g., Alzheimer's disease, multiple sclerosis, Parkinson's disease, amyotrophic lateral sclerosis, Creutzfeldt-Jakob disease), stroke, epilepsy, and brain trauma.

The Kallikrein-Kinin System (KKS)

Figure 1:
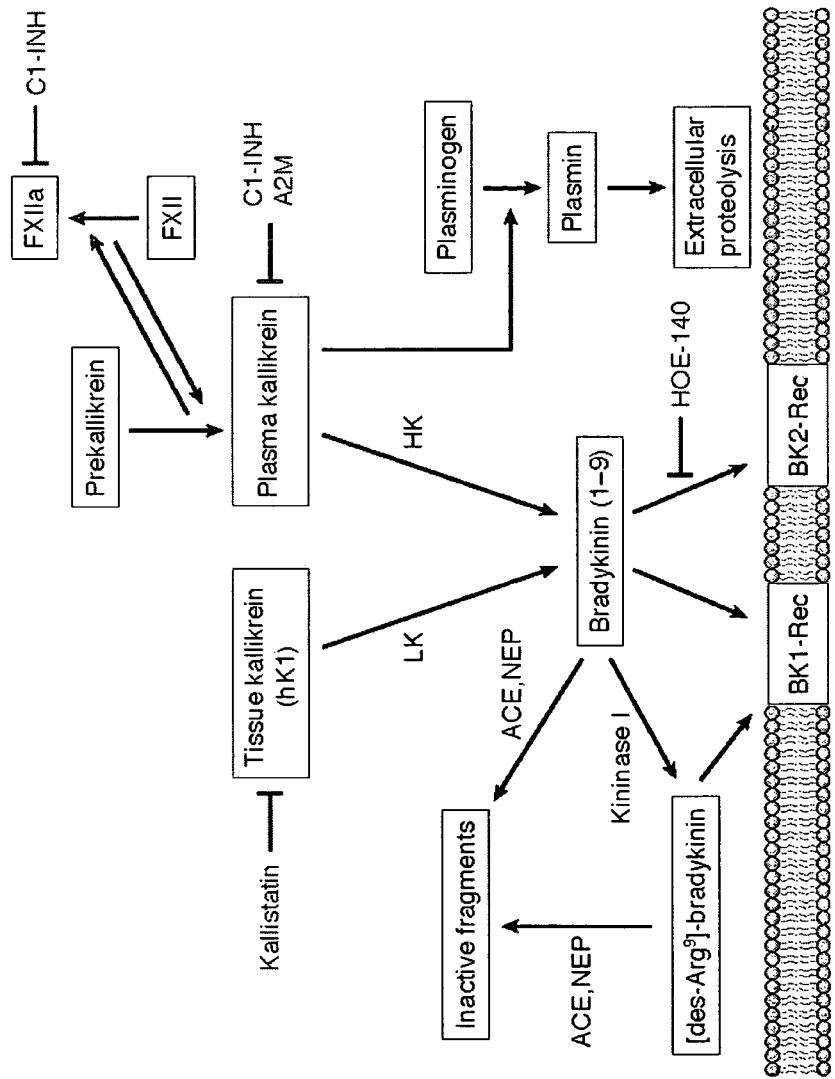
FIG. 1 is a diagram showing the role of the plasma kallikrein-kinin system (KKS) in retinal edema. Diabetes increases the actions of kallikrein on the retina and the adverse effects of kallikrein on retinal vascular permeability and edema are mediated by both the bradykinin type 2 receptor (B2-R) and bradykinin-independent pathways of kallikrein action.

Kallikreins are serine proteases present in biological fluids and tissues. They are divided into plasma and tissue kallikreins that differ in structural characteristics and function. Increased plasma kallikrein activity induces cleavage of factor XII to factor XIIa, which initiates the positive feedback activation of the contact system (FIG. 1). Factor XIIa activates factor XI, and thereby triggers intrinsic coagulation. Activated plasma kallikrein enzymatically mediates the release of bradykinin (BK) from its precursor high molecular weight kininogen (HK; FIG. 1). The binding of bradykinin to $B_1$ or $B_2$ receptors initiates signaling through nitric oxide-cGMP and prostacyclin-cAMP and results in a wide spectrum of actions as part of the inflammatory response that develops after tissue injury.

All components of the kallikrein-kinin system have been identified in the brain of various species including humans (Regoli et al., *Immunopharmacol.* 36:143-147 (1997)). $B_2$ receptors have been reported to be located on cultured astrocytes (Cholewinski et al., *J. Neurochem.* 57:1456-1458 (1991); Gimpl et al., *Neurosci. Lett.* 144:139-142 (1992)), oligodendrocytes (Hess et al., *Biochem. Biophys. Res. Commun.* 184:260-268 (1992)), microglia (Noda et al., *Life. Sci.* 72:1573-1581 (2003)), and on cerebral endothelial cells. A constitutive expression of cerebral $B_2$ receptors has been confirmed in cortical and striatal neurons, which both belong to brain areas severely affected after a focal cerebral injury (Chen et al., *J. Comp. Neurol.* 427:1-18 (2000); Raidoo et al., *J. Neuroimmunol.* 77:39-44 (1997)). $B_2$ receptor activation induces the release of inflammatory mediators such as reactive oxygen radicals (Sobey, Br. *J. Pharmacol.* 139:1369-1371 (2003)), nitric oxide (Regoli et al., *Immunopharmacol.* 33:24-31 (1996)), prostanoids (Easton et al., *Brain Res.* 953: 157-169 (2002)), and cytokines (Schwaninger et al., *J. Neurochem.* 73:1461-1466 (1999)). This release ultimately leads to increases in vascular permeability, blood-brain barrier (BBB) disruption, and cerebral edema (Plesnila et al., J. Neurotrauma. 18:1049-1058 (2001); Unterberg et al., *J. Cereb. Blood Flow. Metab.* 4:574-585 (1984); Ellis et al., *Stroke* 18:792-795 (1987); Kamitani et al., *Circ. Res.* 57:545-552 (1985); Relton et al., *Stroke* 28:1430-1436 (1997)). A number of experimental studies have shown that $B_2$ receptor blockade in a focal cerebral ischemia model improved neurological outcome, reduced infarct volume, and attenuated the development of brain edema (Relton et al., *Stroke* 28:1430-1436 (1997); Ding-Zhou et al., *Br. J. Pharmacol.* 139:1539-1547 (2003); Lumenta et al., *Brain Res.* 1069:227-234 (2006)), indicating bradykinin aggravates cerebral injury at an early stage. Controversially, Chao et al. have reported that delayed kallikrein gene delivery protects against ischemia/reperfusion induced neurological dysfunction and cerebral infarct size in rats after middle cerebral artery occlusion, and icatibant abrogated these effects (Xia et al., *Hum. Gene Ther.* 17:206-219 (2006); Xia et al., *Hypertension* 47:752-761 (2006); Chao et al., *Front. Biosci.* 11:1323-1327 (2006)). A possible explanation for the differential effects of early versus late interventions is that the timing of brain inflammation occurs within several days after stroke, including early injury and late postischemic repair processes (Xia et al., *Hypertension* 47:752-761 (2006)). C1-Esterase inhibitor (C1-INH), belonging to the superfamily of serine proteinase inhibitors (serpins), is a major inhibitor of the classical complement pathway, the contact activation system, and the intrinsic pathway of coagulation. Systemic delivery of C1-INH has been shown to successfully reduce edema in a growing number of both human and animal studies (Akita et al., *Neurosurgery* 52:395-400 (2003); Caliezi et al., *Pharmacol. Rev.* 52:91-112 (2000); Han et al., *J. Clin. Invest.* 109:1057-1063 (2002); De Simoni et al., *J. Cereb. Blood Flow. Metab.* 23:232-239 (2003)).

In addition to the well-characterized actions mediated via bradykinin (FIG. 1), plasma kallikrein has also been shown to activate the zymogen plasminogen to its active form, plasmin, in urokinase (uPA) and tissue plasminogen activator (tPA) double-deficient mice (Lund et al., *EMBO J.* 25:2686-2697 (2006); Selvarajan et al., *Nat. Cell Biol.* 3:267-275 (2001)). These interesting findings suggest that kallikrein exerts actions via plasmin, which plays a central role in fibrinolysis and the activation of metalloproteinases (MMP; Liu et al., *J. Clin. Invest.* 115:879-887 (2005)). Several interactions between the plasminogen/plasmin and MMP systems suggest that both systems may cooperate in achieving extracellular matrix degradation. In cerebral ischemia, both MMP-9 and MMP-3 are increased in the ischemic area (Tsuji et al., *Stroke* 36:1954-1959 (2005); Suzuki et al., *J. Thromb. Haemost.* 5:1732-1739 (2007)). MMP-9 has been implicated in various injury mechanisms after cerebral ischemia, such as brain edema, hemorrhagic transformation, and the accentuation of cell death. Thus, the kallikrein-plasmin-MMP-9 pathway might play an important role in cerebral vascular proteolysis in stroke. In view of these results, we believe that inhibition of the KKS system using the compound described herein may be useful in treatment or prevention of these diseases or conditions.

The KKS in Inflammatory Pathways

Activation of the KKS has been shown to induce a host of pro-inflammatory responses. B1 receptor expression is increased in the retina of rats with STZ induced diabetes (Abdouh et al., *Br. J. Pharmacol.* 140:33-40 (2003)), and activation of NF-κβ upregulates B1 receptor expression (Sabourin et al., *Am. J. Physiol. Heart Circ. Physiol.* 283:H227-H237 (2002)). Bradykinin has also been demonstrated to cause leukostasis (Shigematsu et al., *Am. J. Physiol. Heart Circ. Physiol.* 283:H2676-H2686 (2002); Bloechle et al., *Am. J. Physiol.* 274:G42-G51 (1998)), possibly via a mechanism that involves bradykinin-induced superoxide formation (Shigematsu et al., (2002)). Moreover, pro-inflammatory cytokines can up regulate the B1 receptor (Ni et al., *J. Biol. Chem.* 273:2784-2791 (1998)). Expression of the B1 receptor is increased in lipopolysaccharide (LPS)-induced vascular smooth muscle cells via an NF-κβ-like nuclear factor (Ni et al., supra (1998)). An absence of B1 receptors results in decreased inflammatory responses to LPS, including a decrease in leukostasis (Pesquero et al., *Proc Natl. Acad. Sci.* (*USA*) 97:8140-8145 (2000)), and mice over-expressing the B1 receptor display increased susceptibility to paw edema (Ni et al., *J. Biol. Chem.* 278:219-225 (2003)), confirming that this receptor plays a central role in the initiation and modulation of inflammation. Accordingly, a compound of formula I or formula II may be used to inhibit the KKS and to reduce inflammatory responses.

The KKS in Vascular Permeability

Bradykinin, via nitric oxide, induces vasorelaxation of isolated retinal arterioles, providing evidence for the direct effects of bradykinin on the retinal vasculature (Jeppesen et al., *Invest. Ophthalmol. Vis. Sci.* 43:1891-1896 (2002)). The B1 receptor has been attributed to many of the pro-inflammatory actions of bradykinin, and increased B1 receptor expression occurs in the diabetic retina (Lawson et al., *Regul. Pept.* 124:221-224 (2005); Abdouh et al., *Br. J. Pharmacol.* 140: 33-40 (2003)). Kallikrein-binding protein, a serpin inhibitor of tissue kallikrein, can reduced RVP in diabetic rats (Gao et al., *Diabetologia* 46:689-698 (2003)), suggesting a role of tissue kallikrein. However, kallikrein-binding protein does not inhibit plasma kallikrein, and therefore would not be expected to affect the contact system. Transgenic expression of wild-type and constitutively active B1 receptors increased vascular permeability, blood pressure, and susceptibility to inflammation (Ni et al., *J. Biol. Chem.* 278:219-225 (2003)), directly establishing the pro-inflammatory role of the B1 receptors. While bradykinin receptors exert a number of effects on vascular homeostasis and innate inflammation, presently available data from recent clinical trials to treat angioedema have shown that elevated levels of bradykinin are associated with vasogenic edema (Nussberger et al., *Lancet.* 351:1693-1697 (1998)), whereas kallikrein inhibitors or bradykinin antagonists reduce edema symptoms (Bork et al., *J. Allergy. Clin. Immunol.* 119:1497-1503 (2007); Schneider et al., *J. Allergy. Clin. Immunol.* 120:416-422 (2007)).

The KKS in Angiogenesis

The kallikrein/bradykinin pathway has been shown to play an important role in both hind limb and tumor angiogenesis. Ischemia-induced neovascularization caused by hind limb injury is impaired in bradykinin receptor B2-R and in B1-R knockout mice (Emanueli et al., *Circulation* 105:60-366 (2002); Ebrahimian et al. *Arterioscler. Thromb. Vasc. Biol.* 25:65-70 (2005)). Treatment of mice with an anti-HK antibody, which inhibits its processing by kallikrein to release BK, reduced tumor angiogenesis (Song et al., *Blood* 104: 2065-2072 (2004)). Conversely, over expression of tissue kallikrein in mice with hind limb ischemia using an adenoviral vector increased angiogenesis (Emanueli et al., *Circulation*. 103:125-132 (2001)). The mechanism of kinin-induced angiogenesis includes the transactivation of the VEGF/KDR pathway. Stimulation of cultured endothelial cells with bradykinin results in the rapid transactivation of VEGF receptors (KDR; Thuringer et al., *J. Biol. Chem.* 277:2028-2032 (2002); Miura et al., *Hypertension.* 41:1118-1123 (2003)). This bradykinin response is blocked by Hoe140, a selective B2-R antagonist, suggesting that this crosstalk is mediated by the B2 receptor. The kallikrein/bradykinin pathway appears to play a role in the neovascularization in the retina. Indeed, a single intravitreal injection of kallikrein-binding protein (KBP), an endogenous inhibitor of tissue kallikrein, reduced oxygen-induced retinopathy (OIR) in Brown Norway rats (Gao et al., *Diabetologia* 46:689-698 (2003)). However, the anti-angiogenic effect of KBP has been attributed to its heparin-binding domain, which interferes with VEGF binding to its receptor (Miao et al., *Am. J. Physiol. Cell Physiol.* 284: C1604-C1613 (2003)). Inhibition the kallikrein-kinin system, e.g., by administration of a compound of formula I or formula II, may reduce neovascularization in proliferative diabetic retinopathy (PDR), and may reduce transactivation of VEGF-R2.

The KKS and Stroke in Diabetes Mellitus (DM), Type 1

The kallikrein-kinin system is activated in both animal models and humans during stroke and kinin antagonists reduce edema formation (Storini et al., *J. Pharmacol. Exp. Ther.* 318:849-854 (2006); Akita et al., *Neurosurgery* 52:395-400 (2003); Relton et al., *Stroke* 28:1430-1436 (1997); Wagner et al., *J. Neurol. Sci.* 202:75-76 (2002)). Moreover, extracellular carbonic anhydrase-1 (CA-1) induces RVP and decreases edema by blocking the kallikrein-kinin pathway at multiple levels (Gao et al., *Nat. Med.* 13:181-188 (2007)).

Intracerebral hemorrhage induced by autologous blood is increased in rats with streptozotocin (STZ)-induced diabetes and treatment of rats systemically with a novel small molecular inhibitor of plasma kallikrein reduces subarachnoid hematoma expansion in diabetic rats. These findings illustrate a role for plasma kallikrein in the exacerbation of cerebral vascular injury in DM, and suggest that compounds of formula I or formula II may be useful in the treating the systems or reducing the damage associated with hemorrhagic stroke.

Diabetic Retinopathy

Proliferative diabetic retinopathy (PDR) is a leading cause of vision loss in working-age adults. Our studies illustrate that the kallikrein-kinin pathway can contribute to the transformation from increased retinal vascular permeability (RVP), which has been widely studied in rodent models of diabetes (Miyamoto et al., *Proc. Natl. Acad. Sci.* (*USA*) 96:10836-10841 (1999); Miyamoto et al., *Am. J. Pathol.* 156:1733-1739 (2000); Barber et al., *Invest. Ophthalmol. Vis. Sci.* 46:2210-2218 (2005); Aiello et al., *Diabetes* 46:1473-1480 (1997)), to retinal thickening (Gao et al., *Nat. Med.* 13:181-188 (2007)) that is similar to the clinically-evident retinal edema in diabetes.

Using mass spectroscopy-based proteomics, we have characterized the human vitreous proteome from three groups of people: non-diabetics (NDM), diabetics without diabetic retinopathy (noDR), and diabetics with PDR. This study revealed that hemorrhage, which commonly occurs in both PDR and non-proliferative diabetic retinopathy (NDPR), modifies the vitreous proteome, resulting in a 15-fold increase in extracellular carbonic anhydrase-I (CA-I) in vitreous from individuals with PDR and NPDR, compared with NDM and noDR.

Our results show that intravitreal injection of CA-I in rats results in a rapid increase in RVP and that this response is mediated by the activation of intraocular plasma kallikrein. We demonstrate that the three main components of the plasma kallikrein-kinin system (KKS), namely plasma kallikrein, factor XII (FXII), and high molecular weight kininogen (HK), are present in their activated forms in the vitreous of people with PDR. The rapid increase in RVP induced by CA-I was followed by the development of focal areas of increased RVP to large molecules, including fluorescein-labeled $2 \times 10^6$ Da-dextran conjugate, which were evident 48 hours after a single intravitreal injection of CA-I. In addition, in the context of diabetes, CA-I caused intraretinal thickening at this time point. We have demonstrated that CA-I-induced retinal edema is decreased by complement 1 inhibitor, neutralizing antibody to prekallikrein, and bradykinin receptor antagonism, which blocks the kallikrein-kinin pathway at multiple levels. These results suggest that components of the KKS could serve as therapeutic targets for the treatment of DR, and that inhibition of the KKS by a compound of formula I or formula II may be a useful strategy in treatment of diabetic retinopathy.

Astrocyte abnormalities has also been observed in DR. See, for example, Nishikiori et al., *Diabetes* 56:1333-1340, (2007), Gardner et al., *Invest. Ophthalmol. Vis. Sci.* 38:2423-2427 (1997), and Barber et al., *Invest. Ophthalmol. Vis. Sci.* 46:2210-2218 (2005).

Diabetic Macular Edema

Diabetic macular edema (DME) is the most prevalent cause of vision loss in patients with diabetes mellitus. The condition is characterized by diffusion of serum proteins and lipids across the retinal endothelium into the intraretinal space, resulting in fluid retention, lipid deposition, and thickening of the macula. Vision can be transiently or permanently reduced.

The inability of the retina to compensate for this excessive increase in RVP may be a primary cause of DME, which occurs most frequently in patients with advanced stages of DR. Since DME occurs in patients with NPDR, active PDR, or quiescent PDR (QPDR), the factors that cause intraretinal edema appear to be, at least in part, distinct from those that cause retinal neovascularization. The retinal vascular endothelium provides an essential role in maintaining the composition of both the retinal interstitial fluid and the vitreous fluid. An increase in retinal vascular permeability (RVP) is observed in early diabetes and there is an additional increase in RVP that correlates with the severity of DR. Reports from our group and others have demonstrated that hormones and growth factors that contribute to PDR are present in the vitreous (Aiello et al., *N. Engl. J. Med.* 331:1480-1487 (1994); Funatsu et al., *Ophthalmol.* 110:1690-1696 (2003); Funatsu et al., *Am. J. Ophthalmol.* 133:537-543 (2002); Simo et al., *Diabetes Care.* 27:287-288 (2004); Simo et *Clin. Sci.* (Lond.) 104:223-230 (2003); Adamis et al., *Am. J. Ophthalmol.* 118:445-450 (1994); Adamis et al., *Am. J. Ophthalmol.* 118:445-450 (1994)). The vitreous may also contain anti-angiogenic and anti-permeability factors, such as pigment epithelium-derived factor (PEDF) and angiostatin, which suppress or oppose the effects of vascular endothelial growth factor (VEGF; King et al., *N. Engl. J. Med.* 342:349-351 (2000); Ogata et al., *Am. J. Ophthalmol.* 134:348-353 (2002); Raisler et al., *Proc. Natl. Acad. Sci.* (*USA*) 99:8909-8914 (2002); Dawson et al., *Science.* 285:245-248 (1999); Spranger et al., *Diabetologia.* 43:1404-1407 (2000)). While VEGF and vascular permeability factor (VPF) contribute to the increase in RVP in DM (Qaum et al., *Invest. Ophthalmol. Vis. Sci.* 42:2408-2413 (2001)) and other conditions such as age-related macular degeneration (Funatsu et al., *Ophthalmol.* 112:806-816 (2005); Gragoudas et al., *N. Engl. J. Med.* 351:2805-2816 (2004)), it does not appear to fully explain the high level of vascular permeability that occur in advanced DR (Aiello et al., *N. Engl. J. Med.* 331:1480-1487 (1994)). Indeed, early studies indicate that intravitreal injection with bevacizumab may not be sufficient to resolve DME (Arevalo et al., *Ophthalmol.* 114:743-750 (2007); Yanyali et al., *Am. J. Ophthalmol.* 144:124-126 (2007)).

While VEGF levels are elevated in PDR, this condition is not always associated with DME. Moreover, DME can occur in people with NPDR and quiescent PDR, which are not conditions typically associated with increased VEGF (Aiello et al., *N. Engl. J. Med.* 331:1480-1487 (1994)). Although intensive glycemic control can reduce the incidence of DME, this approach has not eradicated this condition. The activation of the KKS contributes to retinal inflammation, including RVP and leukostasis, and edema. We present results showing that kallikrein-induced RVP is increased in diabetic rats and mice, compared with non-diabetic controls. This illustrates why intraocular kallikrein activation in the context of diabetes is able to increase retinal thickening in diabetic rats, whereas neither diabetes alone nor kallikrein alone produced this thickening (Gao et al., *Nat. Med.* 13:181-188 (2007)). Thus inhibition of kallikrein activity in a subject suffering from DME, e.g., by administration of a compounds of formula I or formula II, may be useful to treat this disorder.

Preparation of Compounds

Various synthetic routes can be used by a skilled artisan to prepare the compounds of formula I or formula II, and related intermediates, for use in the present invention. The scheme below provides a synthetic route that can be followed to access certain compounds of the present invention. Other routes or modification of the route shown would be readily apparent to a skilled artisan and within the scope of the present invention.

Scheme 1 shows one synthetic approach to the PK-inhibitors of the present invention.

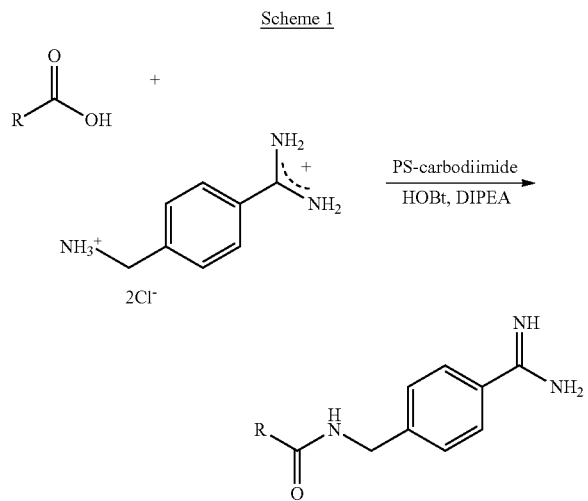

Scheme 1

In Scheme 1, carboxylic acids having various R groups are reacted with amidinobenzylamine in the presence of carbodiimide, HOBt and DIPEA to form carboxylic acid 4-carbamimidoyl-benzylamide derivatives. Amidinobenzylamine was purchased from Astatech, Bristol, Pa. The choice of a particular reaction condition is within the abilities of those skilled in the art.

In a particular example, synthesis of the compounds of this invention is carried out by the formation of a single amide bond between commercially available carboxylic acids (obtained from either ASDI, Inc., or Enamine, Inc., Kiev, Ukraine) and 4-amidino-benzylamine (4-AmBz, obtained from Astatech, Inc., Bristol, Pa.), using PS-Carbodiimide (obtained from Biotage, Inc., Charlottesville, Va.), and synthesis protocols supplied by Biotage. For each synthesis, 100 μmol of PS-carbodiimide is mixed with a separate carboxylic acid (75 μmol), 4-AmBz.2HCl (75 μmol), N-hydroxybenzotriazole (HOBt; 75 μmol) and diisopropylethylamine (DIPEA; 75 μmol), in 4 ml of 40% dimethylsulfoxide (DMSO)/60% dichloromethane (DCM), in a fitted, stoppered polypropylene reaction vessel, and mixed on a Adams Nutator for 48-72 h at room temperature. The product is obtained by filtration, followed by removal of the DCM by evaporation. Greater than 95% coupling of the carboxylic acid to the 4-AmBz takes place under these conditions, as determined by measuring the residual amount of uncoupled 4-AmBZ left by quantitation of its free amine functionality with ninhydrin. The compounds of the present invention are then purified using a Waters WCX cartridge. Approximately 50 μmmol of compound are applied to a 250 mg Waters WCX cartridge (pre-washed with 5 ml each of MeOH then water) in 4 ml of 50% DMSO—50% water. The cartridge is then washed with 20 ml of 5% MeOH—95% water, followed by 5 ml of MeOH. The column is then eluted with 10 ml of 5% HCOOH—95% MeOH. The compound is obtained in >95% purity following evaporation of the solvent in a Savant SpeedVac. Product integrity is determined by an analytical LC-MS/MS determination of mass of the product using a Applied Biosystems/MDS SCIEX Q-STAR mass spectrometer, following separation on a Shimadzu VP HPLC system.

Certain compounds prepared and purified using this procedure are listed in Tables 1 and 2 above.

Reducing Vascular Permeability

A compound of formula I or formula II (e.g., any described herein) can be used to decrease vascular permeability in a subject (e.g., to treat a subject having a disease associated with increased vascular permeability, such as those described herein). Risk factors for increases in vascular permeability (e.g., retinal vascular permeability) include diabetes (e.g., type-1 or type-2 diabetes mellitus), hypertension, insulin resistance, ketoacidosis, trauma, infection, certain medications (e.g., angiotensin converting enzyme (ACE) inhibitors, factors that reduce dipeptidyl peptidase IV activity, and thiazolidinediones) and hyperglycemia. Increases in retinal vascular permeability can result in eye diseases such as diabetic retinopathy (e.g., proliferative or nonproliferative retinopathy). Other related disorders include those associated with increased retinal or cerebral vascular permeability or vasogenic edema.

Disorders associated with excessive vascular permeability and/or edema in the eye, e.g., in the retina or vitreous, include age-related macular degeneration (AMD), retinal edema, retinal hemorrhage, vitreous hemorrhage, macular edema (ME) (e.g., diabetic macular edema (DME), clinically significant macular edema (CSME), or cystoid macular edema (CME)), proliferative diabetic retinopathy (PDR) and non-proliferative diabetic retinopathy (DR); radiation retinopathy; telangiectasis; central serous retinopathy; and retinal vein occlusions. Retinal edema is the accumulation of fluid in the intraretinal space. DME is the result of retinal microvascular changes that occur in patients with diabetes. This compromise of the blood-retinal barrier leads to the leakage of plasma constituents into the surrounding retina, resulting in retinal edema. Other disorders of the retina include retinal vein occlusions (e.g., branch or central vein occlusions), radiation retinopathy, sickle cell retinopathy, retinopathy of prematurity, Von Hipple Lindau disease, posterior uveitis, chronic retinal detachment, Irvine Gass Syndrome, Eals disease, retinitis, and choroiditis. Disorders associated with excessive vascular permeability or edema in the brain include cerebral edema (e.g., high altitude edema), intracerebral hemorrhage, subdural hemorrhage, sub-arachnoid hemorrhage, hemorrhagic stroke, and hemorrhagic transformation of ischemic stroke. Cerebral edema is an increase in brain volume caused by an absolute increase in cerebral tissue fluid content; vasogenic cerebral edema arises from transvascular leakage caused by mechanical failure of the endothelial tight junctions of the blood-brain barrier (BBB). In some cases, cerebral edema can be caused by high altitude (e.g., a rapid transition to at least 8,000 ft above sea level).

Proliferative diabetic retinopathy is also associated with increased vascular permeability in the eye and is caused by a breakdown of the blood-retinal barrier, and an increase in vascularization in the eye. This vascularization can result in leakage of blood into the eye, which in turn can lead directly to loss of vision.

Other disorders associated with increased permeability include excessive vascular permeability associated with hypertension or inflammation; increased systemic vascular permeability, e.g., associated with septic shock, scurvy, anaphylaxis, hereditary or acquired angioedema (both of which have been linked to C1 inhibitor deficiency), brain aneurysm, and arterial-venous malformation.

In some embodiments, the disorder associated with increased permeability is also associated with hemorrhage, i.e., bleeding into the affected area. In some embodiments, the disorder associated with increased permeability is also associated with lysis of erythrocytes in the affected area.

A disorder associated with increased permeability may also be associated with an increased volume of fluid in the tissue, e.g., edema. Edema may be caused exposure to high-altitude or may be associated with other pathologies. Generally, the fluid is extracellular.

Reducing Astrocyte Activation

A compound of formula I or formula II (e.g., any compound described herein) can also be used to decrease activation of astrocytes (e.g., to treat a disease associated with increased activation of astrocytes). Increased astrocyte activation and increased immune response has been observed in association with various CNS disorders including stroke, trauma (e.g., due to injury or surgery), growth of a tumor, or neurodegenerative disease (e.g., Alzheimer's disease, multiple sclerosis, Parkinson's disease, amyotrophic lateral sclerosis, Creutzfeldt-Jakob disease). Astrocytes have been implicated as a mediator of inflammatory response in the brain, and there is evidence that inappropriate or excessive inflammatory response can contribute to the symptoms, progression, or pathology of such diseases or conditions (see, e.g., Lucas et al., *Br. J. Pharmacol.* 147:S232-S240 (2006)). Based on the results presented herein, astrocyte activation can be mediated by the kallikrein pathway, as evidenced by ERK kinase phosphorylation. In addition, astrocyte activation can be reduced by inhibition of this pathway. Accordingly, the present invention features administration of the compounds described herein to a subject for reducing astrocyte activation or for treatment of disorders associated with astrocyte activation.

In Alzheimer's disease, for example, increased inflammatory response is observed in brains of patients as compared to non-affected patients. Epidemiological evidence suggests administration of anti-inflammatory agents (NSAIDs) reduces the risk of developing or slows the progress of Alzheimer's disease in some patients (see, e.g., Blasko et al., *Aging Cell* 3:169-176 (2004)), and activation of astrocytes are believed to play a role in this process. Accordingly, it may be possible to prevent, slow the progression of, or even reverse development of neurodegenerative diseases by reducing astrocyte activation.

Formulation of Pharmaceutical Compositions

Compound of formula I or formula II (e.g., any compound described herein such as ASP-440 or ASP-465) may be formulated and administered by any suitable means that results in a concentration of the compound that has a desired therapeutic or biological effect (e.g., any described herein such as reduction of vascular permeability or astrocyte activation, treatment of hemorrhagic stroke, retinopathy, or any of the diseases described herein). The compound may be contained in any appropriate amount in any suitable carrier substance, and is generally present in an amount of 1-95% by weight of the total weight of the composition. The composition may be provided in a dosage form that is suitable for oral, parenteral (e.g., intravenously or intramuscularly), rectal, cutaneous, nasal, vaginal, inhalant, skin (patch), ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the compound to a particular target cell type. Administration of the compound in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, molecular complexes, microspheres, nanoparticles, patches, and liposomes.

Parenteral Compositions

A composition containing a compound of formula I or formula II (e.g., any compound described herein) may be administered parenterally by injection, infusion, or implantation (intraocular, subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

In some embodiments, the composition is especially adapted for administration into or around the eye. For example, a composition can be adapted to be used as eye drops, or injected into the eye, e.g., using peribulbar or intravitreal injection. Such compositions should be sterile and substantially endotoxin-free, and within an acceptable range of pH. Certain preservatives are thought not to be good for the eye, so that in some embodiments a non-preserved formulation is used. Formulation of eye medications is known in the art, see, e.g., Ocular Therapeutics and Drug Delivery: A Multi-Disciplinary Approach, Reddy, Ed. (CRC Press 1995); Kaur and Kanwar, Drug Dev Ind Pharm. 2002 May; 28(5): 473-93; Clinical Ocular Pharmacology, Bartlett et al. (Butterworth-Heinemann; 4th edition (Mar. 15, 2001)); and Ophthalmic Drug Delivery Systems (Drugs and the Pharmaceutical Sciences: a Series of Textbooks and Monographs), Mitra (Marcel Dekker; 2nd Rev&Ex edition (Mar. 1, 2003)).

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Dosages

The dosage of any compound of formula I and formula II (e.g., any compound described herein) depends on several factors, including: the administration method, the condition to be treated or the biological effect desired, the severity of the condition or disease, whether the condition or disease is to be treated or prevented, and the age, weight, and health of the subject to be treated.

With respect to the treatment methods of the invention, it is not intended that the administration of a compound to a subject be limited to a particular mode of administration, dosage, or frequency of dosing; the present invention contemplates all modes of administration, including intramuscular, intraocular, intravenous, intraperitoneal, intravesicular, intraarticular, intralesional, subcutaneous, or any other route sufficient to provide a dose adequate to achieve the desired biological or therapeutic effect. The compound may be administered to the subject in a single dose or in multiple doses. For example, a compound described herein or identified using screening methods of the invention may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compound. For example, the dosage of a compound can be increased if the lower dose does not provide sufficient biological activity (e.g., in the treatment of a disease or condition described herein). Conversely, the dosage of the compound can be decreased, for example, if the disease or condition is reduced or eliminated.

While the attending physician ultimately will decide the appropriate amount and dosage regimen, a therapeutically effective amount of a compound described herein (e.g., ASP-440 or ASP-465), may be, for example, in the range of 0.0035 µg to 20 µg/kg body weight/day or 0.010 µg to 140 µg/kg body weight/week. Desirably a therapeutically effective amount is in the range of 0.025 µg to 10 µg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of 0.05 µg to 20 µg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, or once a month. Furthermore, a therapeutically effective amount of a compound may be, for example, in the range of 100 µg/m$^2$ to 100,000 µg/m$^2$ administered every other day, once weekly, or every other week. In a desirable embodiment, the therapeutically effective amount is in the range of 1000 µg/m$^2$ to 20,000 µg/m$^2$, for example, at least 1000, 1500, 4000, or 14,000 µg/m$^2$ of the compound administered daily, every other day, twice weekly, weekly, or every other week.

The following examples are intended to illustrate rather than limit the invention.

Example 1

Activation of the Kallikrein Pathway Increases Retinal Vascular Permeability

Figures 2A, 2B, 2C, 2D, 2E, 2F:
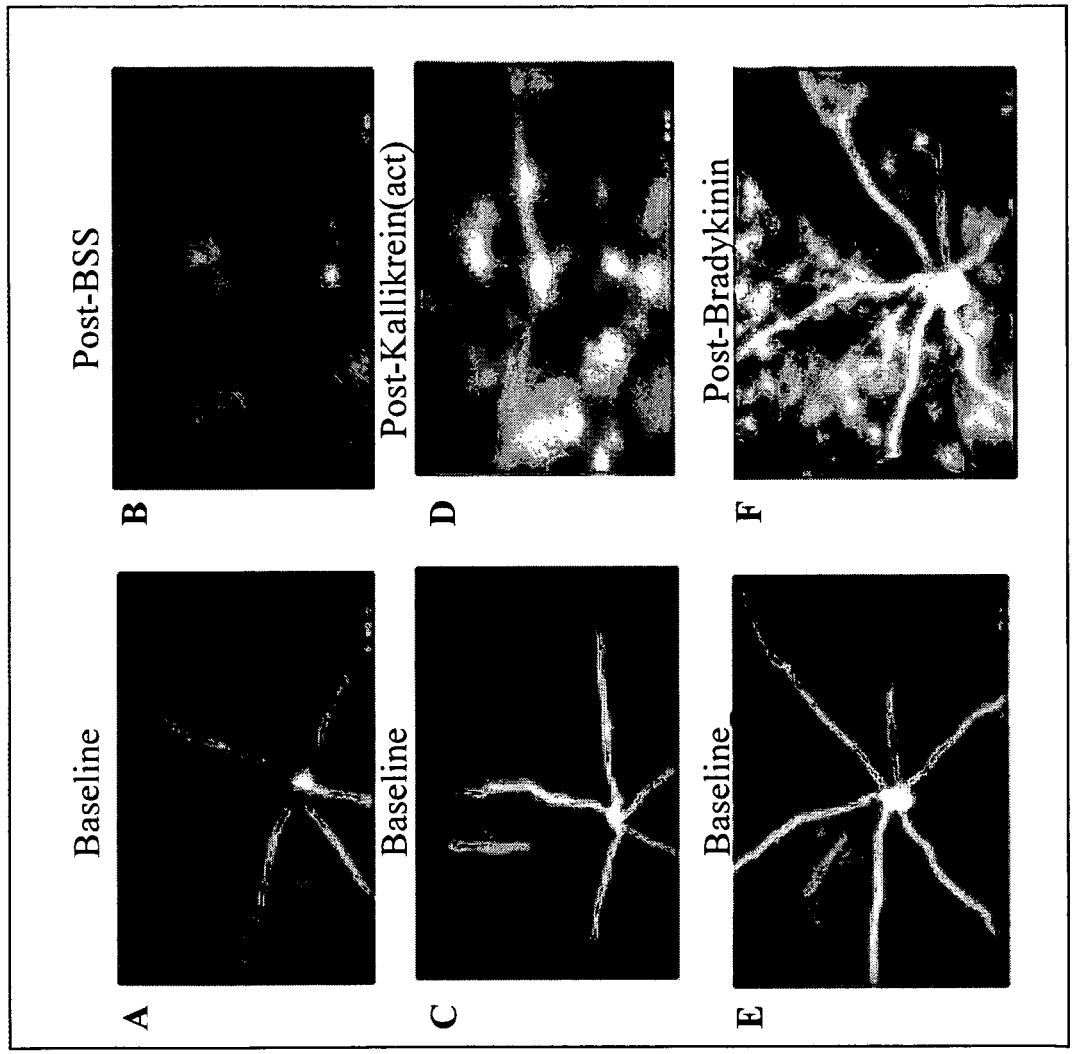
FIGS. 2A-2F are a set of six photomicrographs showing the effects of intravitreal injection of kallikrein and bradykinin on first phase fluorescein retinal vascular leakage visualized by SLO imaging.
Figures 3A, 3B:
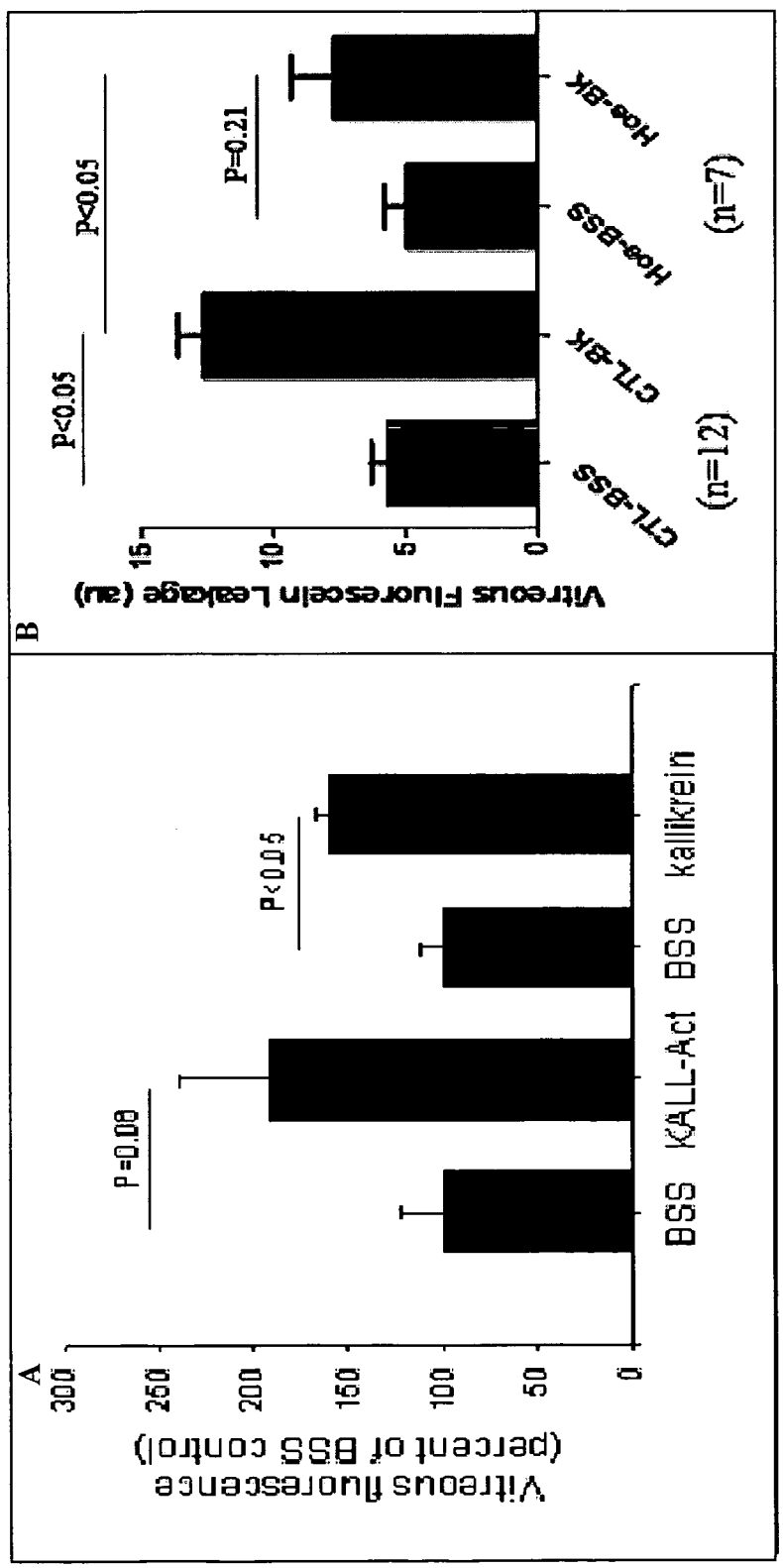
FIGS. 3A-3B are a set of two bar graphs that show the effects of intravitreal injection of kallikrein (FIG. 3A) and bradykinin (FIG. 3B) on RVP in rats measured using vitreous fluorophotometry.
Figures 5A, 5B, 5C, 5D, 5E, 5F:
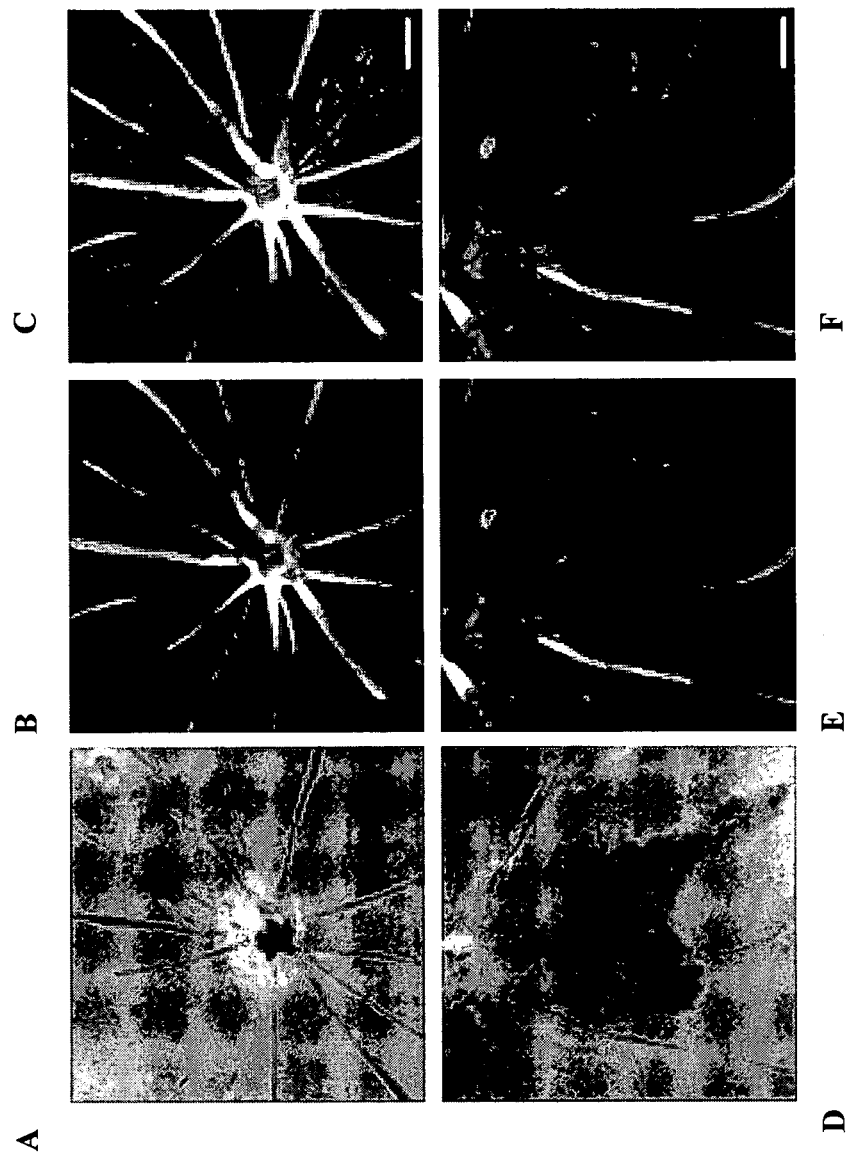
FIGS. 5A-5F are a set of six retinal flatmount images from diabetic rats (2 wks of streptozotocin-induced diabetes) isolated 48 h following intravitreal injection of the contact system, including Factor XII (FXII), high molecular weight kininogen (HK), and plasma kallikrein (PK).

Activators of the kallikrein pathway, including purified activated plasma kallikrein, factor XII (FXII), high molecular weight kininogen (HK), and bradykinin, increase retinal vascular permeability (RVP) to fluorescein. In addition, inhibitors of the kallikrein pathway, such as complement I inhibitors and α2-macroglobulin reduced RVP. Direct injection of these kallikrein pathway activators into the vitreous was observed by SLO fundus imaging of the leakage from first phase fluorescein following bolus intravenous injection (FIG. 2) and by vitreous fluorophotometry, which measure the levels of fluorescein in the vitreous 30 min after intravenous injection (FIG. 5A). RVP is acutely increased by both intravitreal injection of the mixture plasma kallikrein, FXII, and HK (KALL-Act) (FIG. 3A). In addition, intravitreal injection of bradykinin can acutely increase RVP (FIGS. 2A and 2B). Moreover, pretreatment of rats for 2 days with Hoe140 (Bradykinin R2 antagonist, 12 ug/day/200 g rat delivered using a subcutaneous Alzet pump) inhibited bradykinin-induced RVP (FIG. 3B).

Figures 4A, 4B, 4C, 4D:
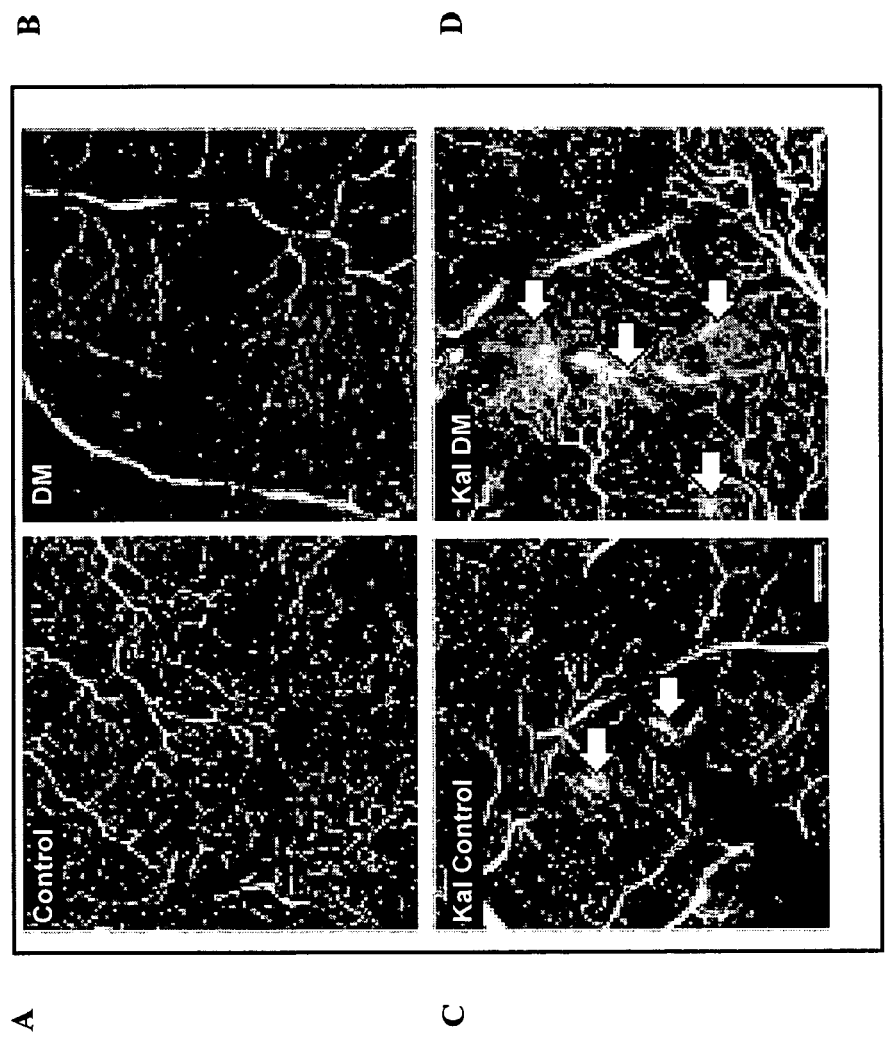
FIGS. 4A-4D are a set of four retina flatmount images showing that kallikrein(act)-induced focal lesions of RVP at 48 h following intravitreal injection are increased in diabetes. Non-diabetic control and 3 wk diabetic rat retina confocal images using FITC dextran.

Performing intravitreal injection of kallikrein induced focal areas of enhanced retinal vascular leakage. The effect of kallikrein was observed on retinal flatmount by confocal fluorescent microscopy of rat retinal flatmounts from rats injected intravenously with fluorescein-labeled 2×10$^6$ Da-dextran (FIG. 4). In addition, the response to intravitreal kallikrein is increased in the retina from rats with 3 weeks of STZ-induced diabetes compared with non-diabetic controls (FIG. 4). Thus, retinas from diabetic rats have increased sensitively to the vascular permeability effects of kallikrein compared with non-diabetic controls. In further studies, intravitreal injection of FXII/HK/PK (KALL-Act) in diabetic rats induced retinal hemorrhage (FIG. 5A). Collectively, these results suggest that a small increase in intravitreal plasma kallikrein can increase RVP (FIG. 4). A larger or more sustained increase in plasma kallikrein action, induced by KALL-ACT, can result in catastrophic failure of blood retinal barrier function (FIG. 5A), leading to retinal hemorrhage. These results suggest that inhibitors of kallikrein may be useful in decreasing retinal permeability.

Example 2

The Kallikrein Inhibitor ASP-465 and ASP-440 Reduces RVP

Figure 6:
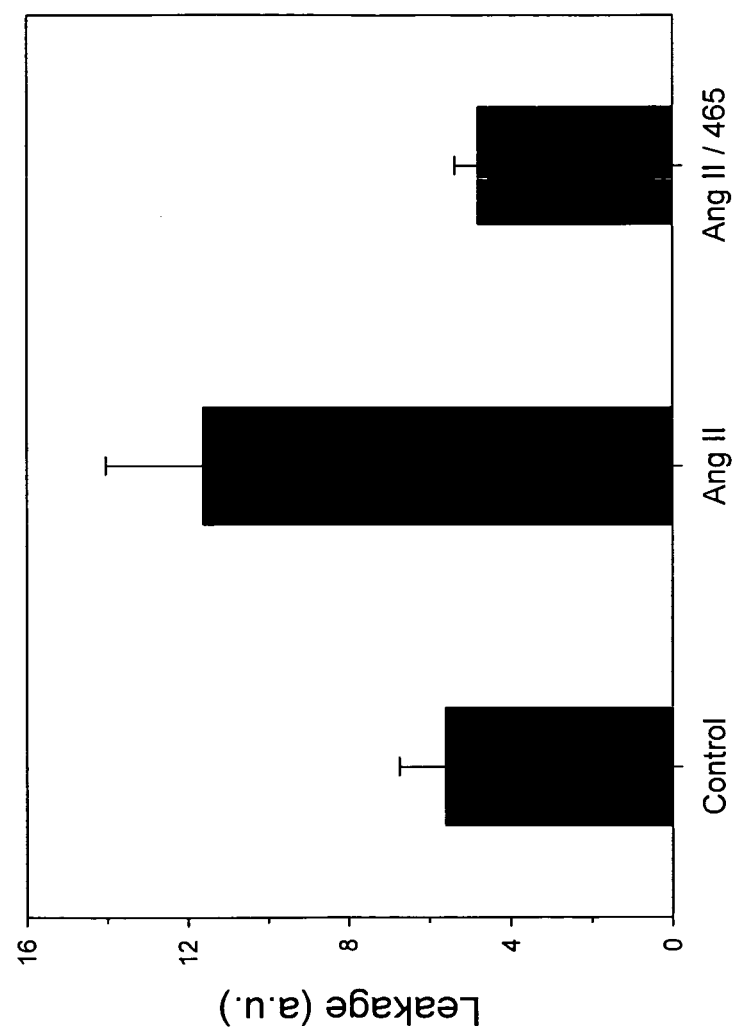
FIG. 6 is a bar graph showing the effect of ASP-465 on AngII-induced retinal vascular permeability. Rats were implanted with a single subcutaneous osmotic pump containing Ang II or two pumps containing AngII and ASP-465, as indicated. RVP was measured using vitreous fluorophotometry after 3 days.
Figure 7:
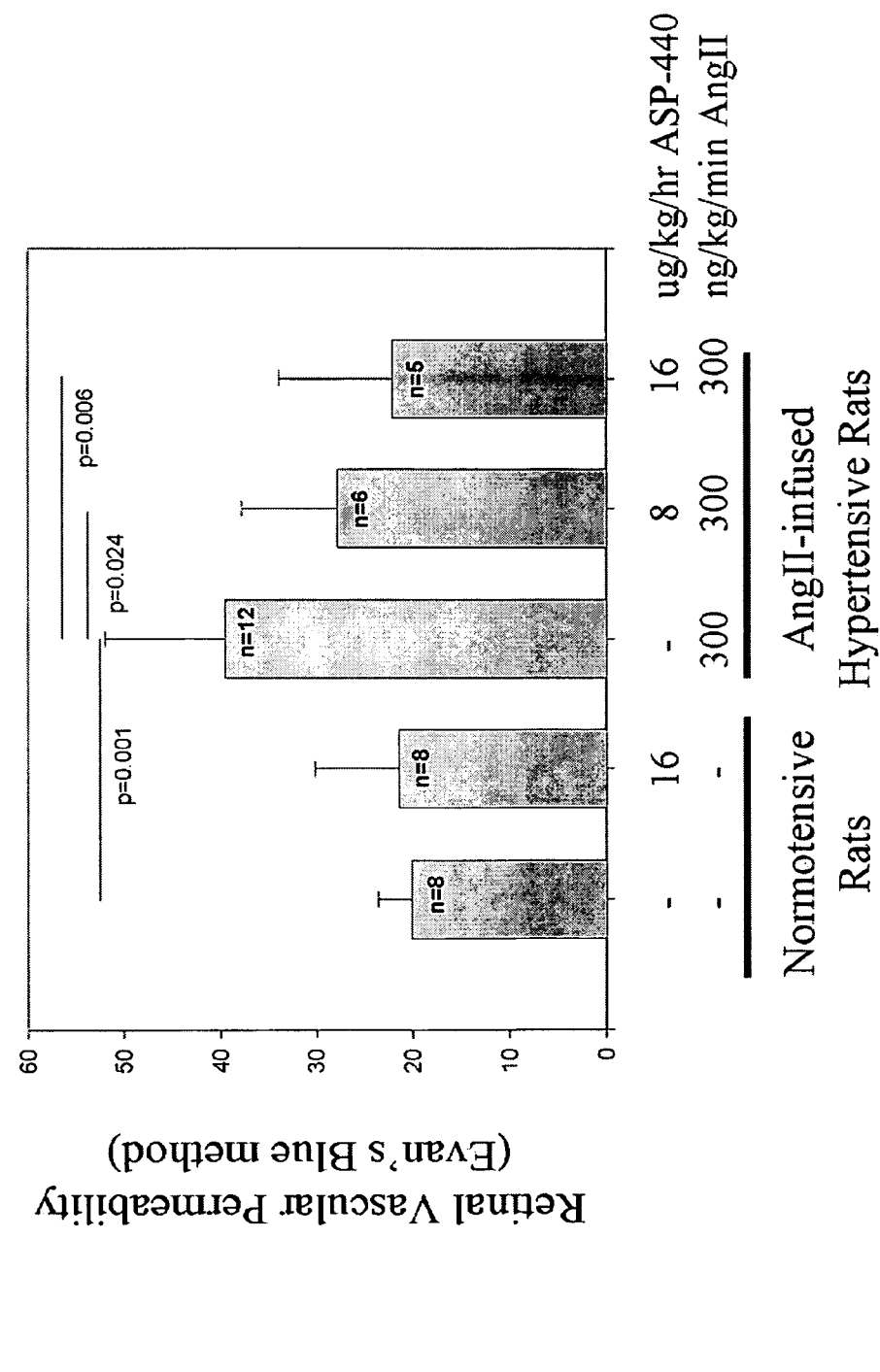
FIG. 7 is a bar graph showing the effect of ASP-440 on AngII-induced retinal vascular permeability. Rats were implanted with a single subcutaneous osmotic pump containing Ang II or two pumps containing AngII and ASP-440, as indicated. RVP was measured using Evan's blue dye method after 7 days.
Figure 8:
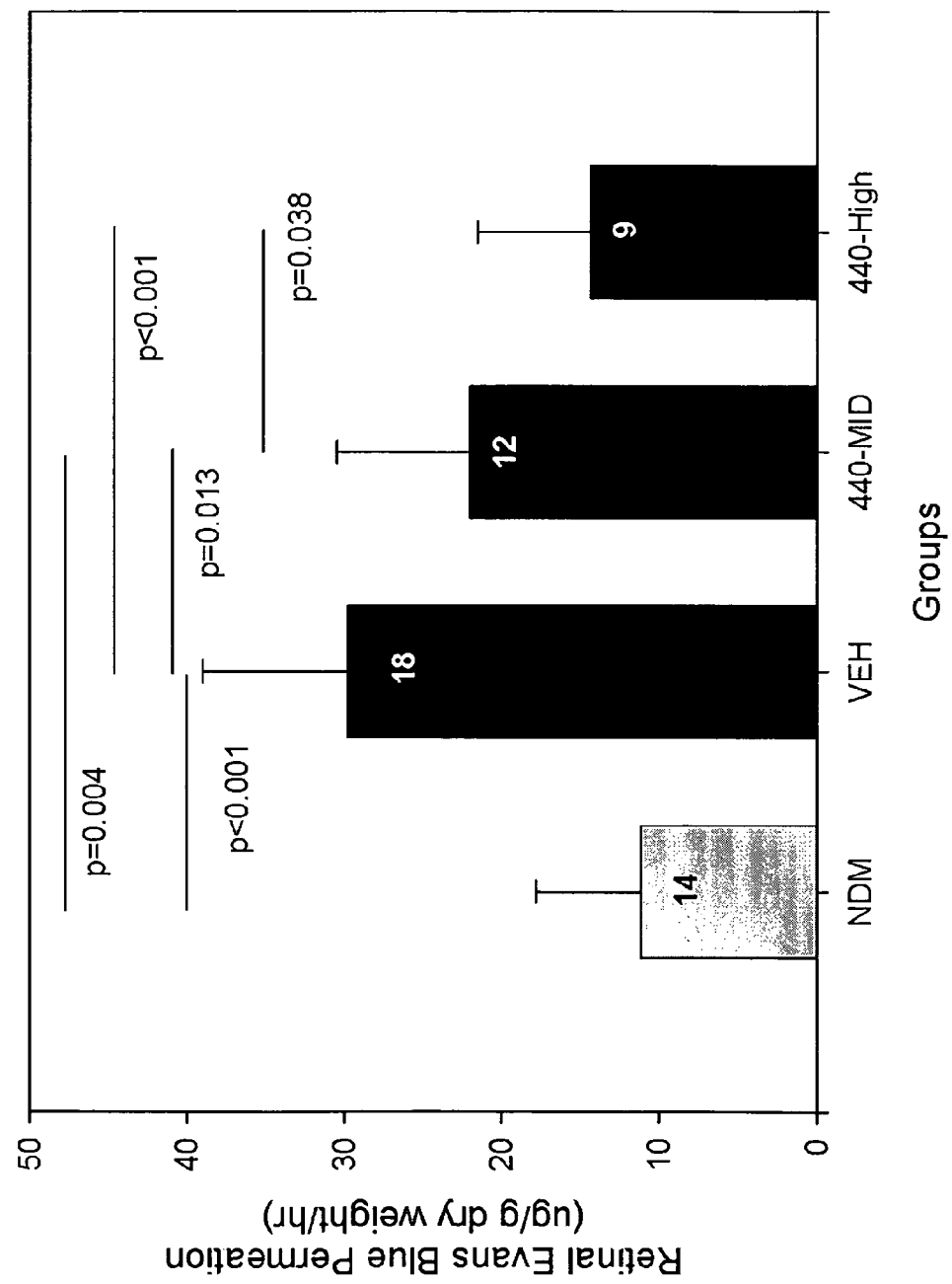
FIG. 8 is a bar graph showing the effect of ASP-440 on diabetes-induced retinal vascular permeability. Rats were implanted with a single subcutaneous osmotic pump containing ASP-440 or vehicle, as indicated. RVP was measured using Evan's blue dye method after 28 days.

We examined the effect of the kallikrein inhibitor ASP-465 on RVP induced by angiotensin II (AngII). Systemic delivery of AngII for 3 days via an Alzet subcutaneous osmotic pump increased systemic blood pressure (data not shown) and increased RVP (FIG. 6). Treatment of rats with both AngII and ASP-465 simultaneously via 2 Alzet pumps for 3 days displayed normal levels of RVP (FIG. 6). Systemic delivery of AngII for 7 days via an Alzet subcutaneous osmotic pump increased systemic blood pressure (data not shown) and increased RVP (FIG. 7). Treatment of rats with both AngII and ASP-440 simultaneously via 2 Alzet pumps for 7 days displayed normal levels of RVP (FIG. 7). Diabetes for 28 days increased RVP, as measured using the Evan's blue dye method (FIG. 8). Treatment of rats with ASP-440 upon confirmation of STZ-induced diabetes displayed normal levels of RVP (FIG. 8). These results suggest that inhibition of plasma kallikrein can reduce RVP, such as that induced by hypertension and diabetes. This suggests an alternative strategy to treat the adverse effects of hypertension and diabetes on the retina. Plasma kallikrein appears to play a fundamental role in plasma extravasation, as illustrated here in the context of the retina. These results indicate that inhibitors of plasma kallikrein activity, as exemplified by ASP-465 and ASP-440, can reduce vascular permeability.

Example 3

Effects on Plasma Kallikrein on Intracellular Signaling in Astrocytes

Figures 9A, 9B:
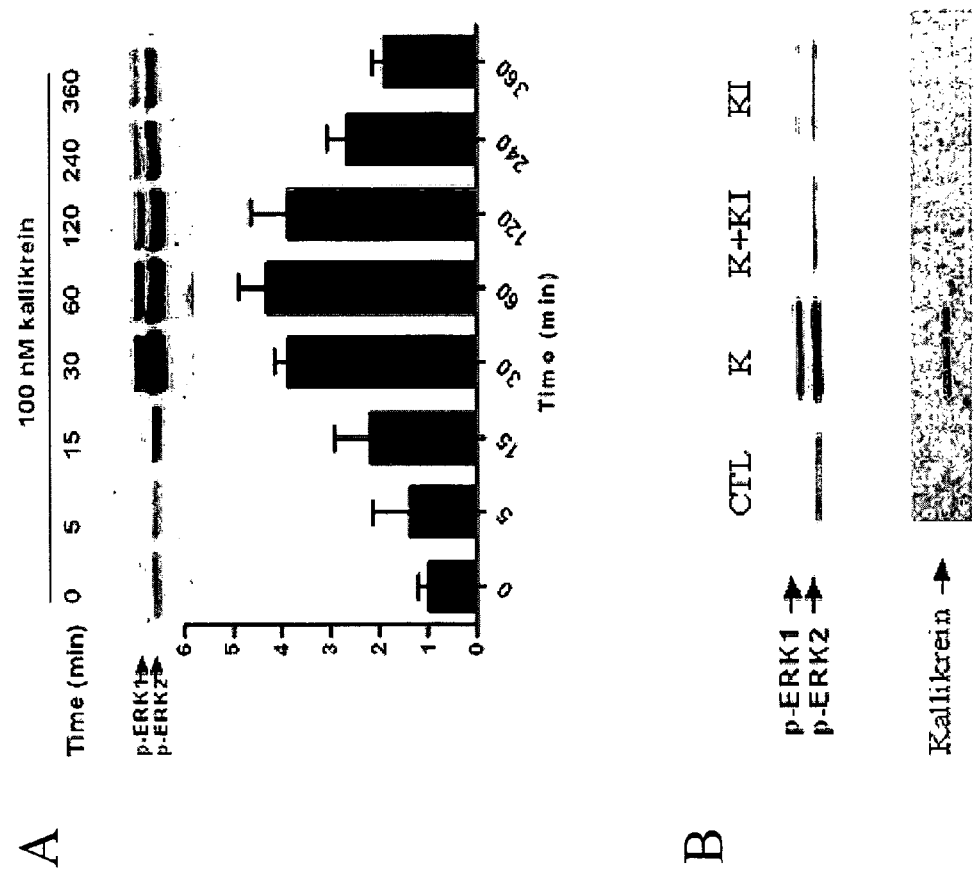
FIGS. 9A-9B are a set of two immunoblots and a bar graph that show the effects of kallikrein (K) and kallikrein inhibitor ASP-440 (KI) on ERK phosphorylation in astrocytes.

We have also studied the effects of plasma kallikrein pathway activation on astrocytes. Bradykinin induces ERK phosphorylation in brain astrocytes and this effect on astrocytes is blocked by Hoe140, indicating that the response is mediated via the bradykinin type 2 receptor (B2-R; data not shown). Exposure of astrocytes to plasma kallikrein potently stimulated ERK phosphorylation, and this action of kallikrein on astrocytes is not affected by B2-R antagonism (Hoe140). The effect of kallikrein on astrocytes was blocked by leupeptin, a protease inhibitor and C1-INH (data not shown). Time course studies demonstrated that plasma kallikrein induced a prolonged activation of ERK, which was sustained for 2 hours (FIG. 9A). This is in contrast to the bradykinin effect, which is rapid and transient (data not shown). Plasma kallikrein's effect on ERK phosphorylation in astrocytes is dose dependent, reaching a maximal effect at 100 nM kallikrein (data not shown). The effect of kallikrein on ERK phosphorylation was blocked by ASP-440 (1-benzyl-1H-pyrazole-4-carboxylic acid 4-carbamimidoyl-benzylamide; FIG. 9B). Interestingly, we found that plasma kallikrein binds to astrocytes. In addition, plasma kallikrein binding to astrocytes was blocked by AS-440 (FIG. 9B) and C1-INH (data not shown). These results indicate that compounds that inhibit plasma kallikrein activity may be useful in reducing astrocyte activation.

Example 4

Effects of Plasma Kallikrein on Extracellular Matrix

Figures 11A, 11B, 11C:
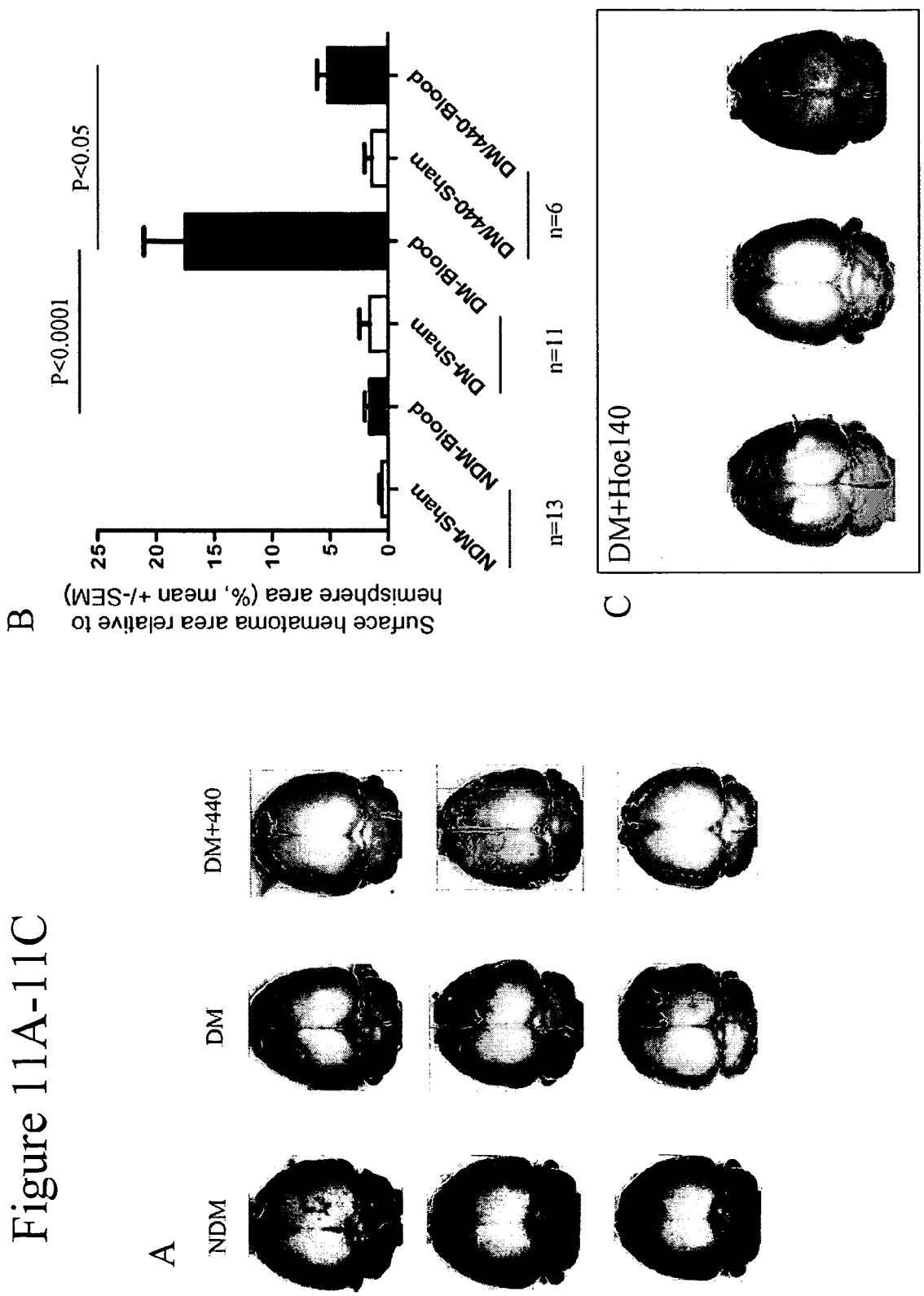
FIGS. 11A-11C are photographs that show the effect of intracerebral infusion of autologous blood (right side) or sham injection (left side) on hematoma area in non-diabetic (NDM) and STZ-induced diabetic (DM) rats in the absence or presence of systemic kallikrein inhibition (ASP-440).

Both bradykinin-dependent and bradykinin-independent mechanisms of action of the kallikrein-kinin system have been described (FIG. 1). The effect of systemic treatment with Icatabant (Hoe 140) on blood-induced hematoma response is shown in FIG. 11C. Surprisingly, Hoe140 treatment did not reduce the blood induced hematoma expansion. These findings indicate that bradykinin-independent effects may contribute to kallikrein's adverse effects on intracerebral hemorrhage, and suggest that kallikrein inhibitors, such as those described herein, can reduce such effects.

Figure 10:
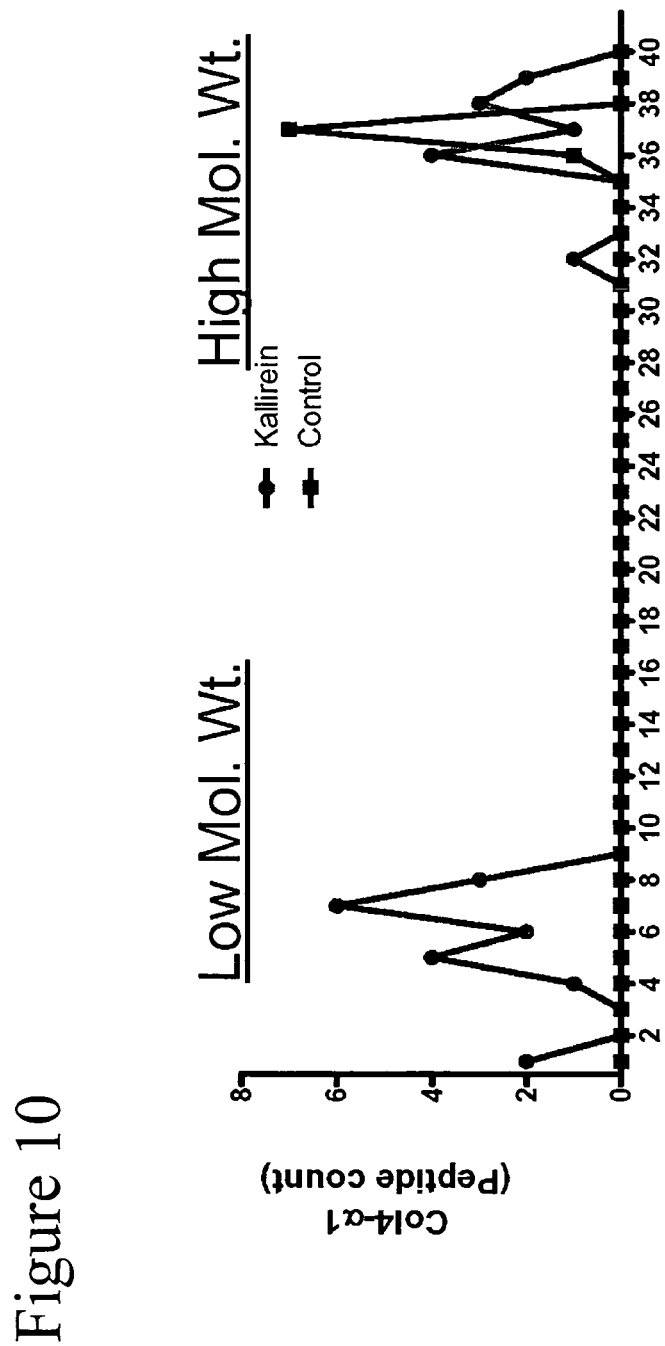
FIG. 10 are bar graphs showing the effect of plasma kallikrein on collagen chain proteolysis of rat brain astrocytes in cell culture. Incubation with purified activated plasma kallikrein releases low molecular weight collagen fragments into the conditioned media.

Further, we performed a proteomic analysis of conditioned media collected from astrocytes cultured in the absence or presence of plasma kallikrein for 24 h. From this analysis, the appearance of low molecular weight fragments of certain collagen chains in conditioned media from plasma kallikrein-treated astrocytes compared with control conditioned media was observed. In particular, kallikrein treatment was associated with an increase in fragments of COL4α1 (FIG. 10) and COL1α2, COL1α1, COL3α1, COL4α2, and COL5α2 (data not shown). These results suggest plasma kallikrein may have a previously unrecognized role in the proteolysis of extracellular matrix proteins present in the basal lamina. Because plasma kallikrein is a highly abundant protease which is activated at the site of vascular injury, the extravasation of plasma kallikrein into the neurovascular unit may weaken the basal lamina. Such weakening may contribute to the hallmark formation of retinal microaneurysms and hemorrhages, which occur and worsen during the progression of non-proliferative diabetic retinopathy.

Example 5

Diabetes Increases Hematoma Expansion Initiated by Intracerebral Injection of Autologous Blood We have compared the response to intracerebral infusion of blood in Sprague-Dawley rats with 1 mo of STZ-induced diabetes with age matched non-diabetic control rats. Fifty µL of autologous whole blood was collected from the tail vein and immediately infused 1 mm anterior, 4 mm lateral and 6 mm in depth to the bregma using a 30 gauge needle at 20 µL per minute. The infusion needle was removed 10 min after injection and the burr hole was sealed with bone wax. Forty-eight hours after intracerebral injection, the animals were perfused with saline and surface hematoma area was examined by measurement of hematoma area relative to total hemisphere area. This study revealed that the hematoma area was significantly increased in rats with 1 mo of diabetes compared with non-diabetic controls (FIG. 11). The contralateral hemisphere received an equivalent injection with saline, which did not induce a hemorrhage. These results show that diabetic rats display an enhanced response to intracerebral injection of blood compared to the response observed in non-diabetic rats.

Further, we tested the effect of a small molecule inhibitor of plasma kallikrein, ASP-440. ASP-440 (1-benzyl-1H-pyrazole-4-carboxylic acid 4-carbamimidoyl-benzylamide; MW=333.4) is a potent ($K_i$=0.1 µM) and specific competitive and reversible inhibitor of purified human plasma kallikrein (PK). The $K_i$ values and predicted inhibition of ASP-440 towards PK and other proteases of the intrinsic and extrinsic coagulation pathways are shown in Table 4.

TABLE 4

Inhibitor profile of ASP-440.

| Enzyme | Ki (µM) | % Inhibition 1 µM | % Inhibition 10 µM |
| --- | --- | --- | --- |
| PlasmaKallikrein | 0.1 | 91 | 99 |
| Factor XIIa | >100 | 0 | 1 |
| Factor XIa | 120 | 0 | 7 |
| Factor IXa | >>100 | 0 | 0 |
| Tissue Factor-Factor VIIa | 160 | 0 | 6 |
| Factor Xa | 85 | 0 | 11 |
| Thrombin | 110 | 1 | 9 |
| Plasmin | 16 | 6 | 38 |

TABLE 4-continued

Inhibitor profile of ASP-440.

| Enzyme | Ki (μM) | % Inhibition @ 1 μM | % Inhibition @ 10 μM |
|---|---|---|---|
| Porcine Pancreatic Kallikrein | >>100 | 0 | 0 |

ASP-440 is also active towards endogenous PK in both human and rat plasmas, with $K_{iapp}$ of 0.2 μM and 0.40 μM, respectively. In keeping with its potency and specificity profile, ASP-440 dose-dependently prolongs coagulation times in plasma by ~50% at 10 μM when plasma is activated with Actin FS reagent (specific activator of the intrinsic coagulation pathway; Dade-Behring), but is without measurable effect on coagulation time when plasma is activated by Innovin reagent (recombinant tissue factor, from Dade-Behring), even at concentrations up to 30 μM.

Rats with 1 mo of diabetes were treated with ASP-440 via a subcutaneous Alzet osmotic pump for 24 h prior to being subjected to the intracerebral infusion of autologous blood. The delivery of ASP-440 was continued during the 48 h period following intracerebral infusion, and hematoma area was assessed as described above. These experiments demonstrated that systemic treatment with ASP-440 reduced hematoma area in diabetic rats to a level comparable to that observed in non-diabetic controls. Accordingly, kallikrein inhibitors, as exemplified by ASP-440, can be used to treat hematoma and related disorders, for example, in diabetic patients.

Example 6

Figure 12:
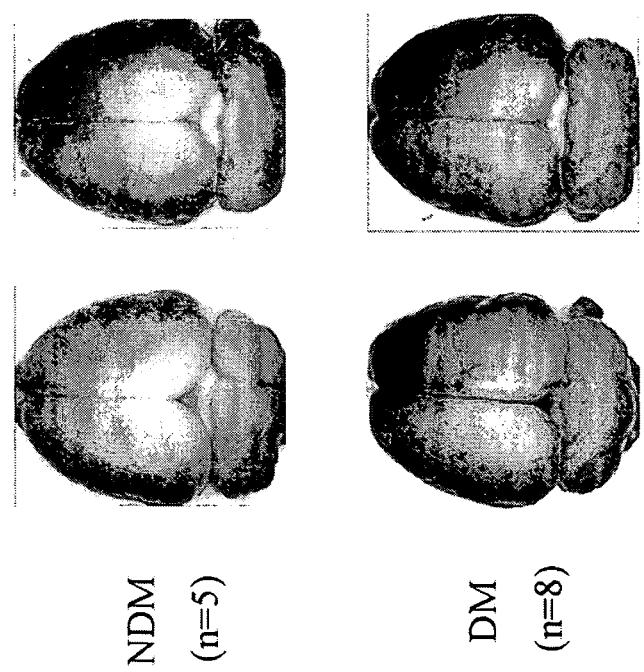
FIG. 12 is a photograph showing the effect of intracerebral infusion of purified activated plasma kallikrein on hematoma area and total hemisphere hemoglobin in non-diabetic (NDM) and STZ-induced diabetic rats.
Figure 13A:
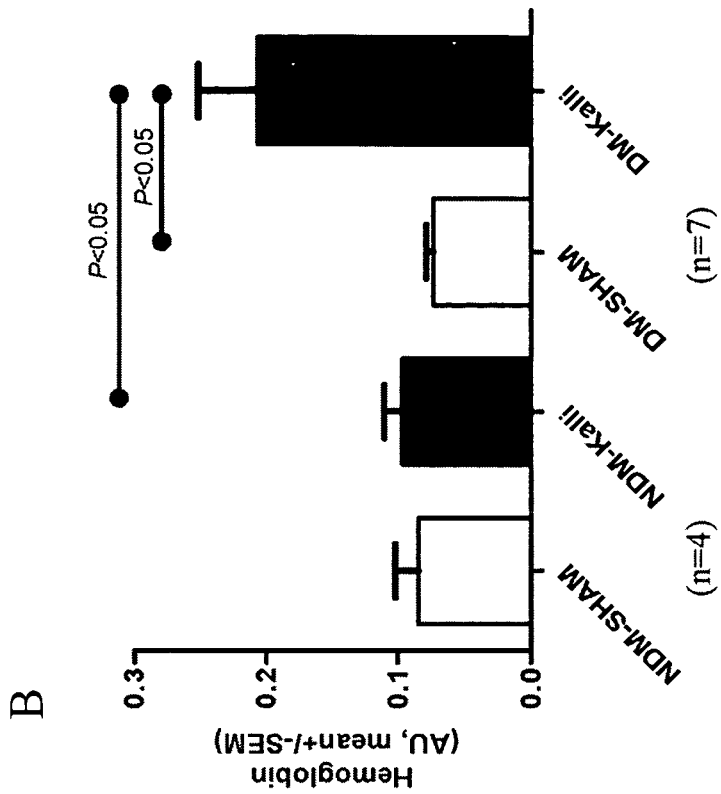
FIGS. 13A-13B are bar graphs showing the effect of intracerebral infusion of purified activated plasma kallikrein on hematoma area (FIG. 13A) and total hemisphere hemoglobin (FIG. 13B) in non-diabetic (NDM) and STZ-induced diabetic rats.
Figure 13B:
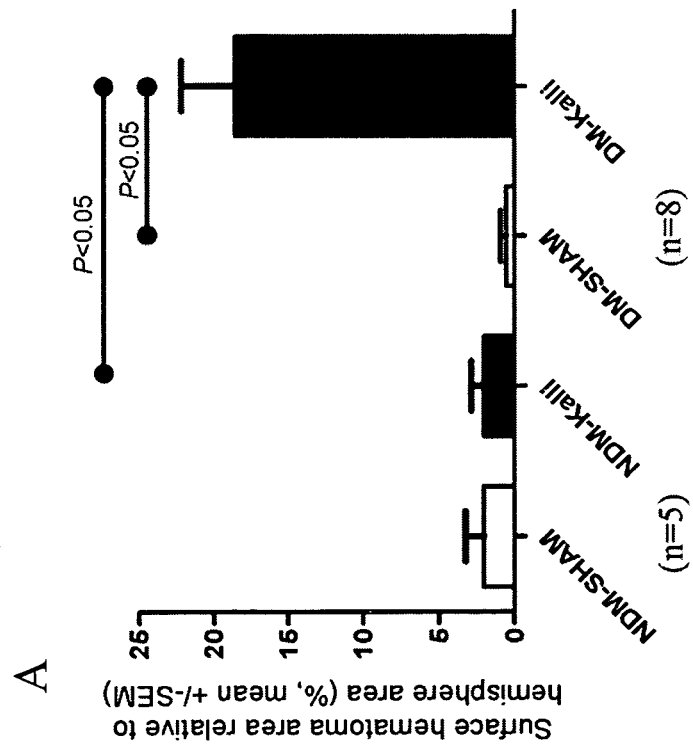

Diabetes Increases Hematoma Response Induced by Activated Plasma Kallikrein The increased response of diabetic rats to the model of intracerebral hemorrhage described above could be due to factors within the blood or due to an increased response in the neurovascular tissue. To evaluate the latter, we performed intracerebral injections of purified activated plasma kallikrein in rats with 1 mo of STZ-induced diabetes or age-matched non-diabetic controls. The contralateral hemisphere was subjected to an equivalent injection with saline vehicle. Rats were sacrificed at 48 h following injection and hematoma area analyzed as described above. We found that the response to plasma kallikrein in diabetic rats was greater than that observed in the non-diabetic controls (FIG. 12). We have found that the increased in hematoma in diabetic rats compared with nondiabetic rats was also observed at 2 hrs following plasma kallikrein injection and this response was decreased by pretreatment of diabetic rats for 24 hrs with ASP-440 via a subcutaneous osmotic pump (data not shown). Moreover, we demonstrated that intracerebral hemorrhage, as measured by heme content and carbonic anhydrase 1 (FIGS. 13A and 13B), in diabetic rats subjected to plasma kallikrein was greater than that observed in non-diabetic controls.

Example 7

Figure 14:
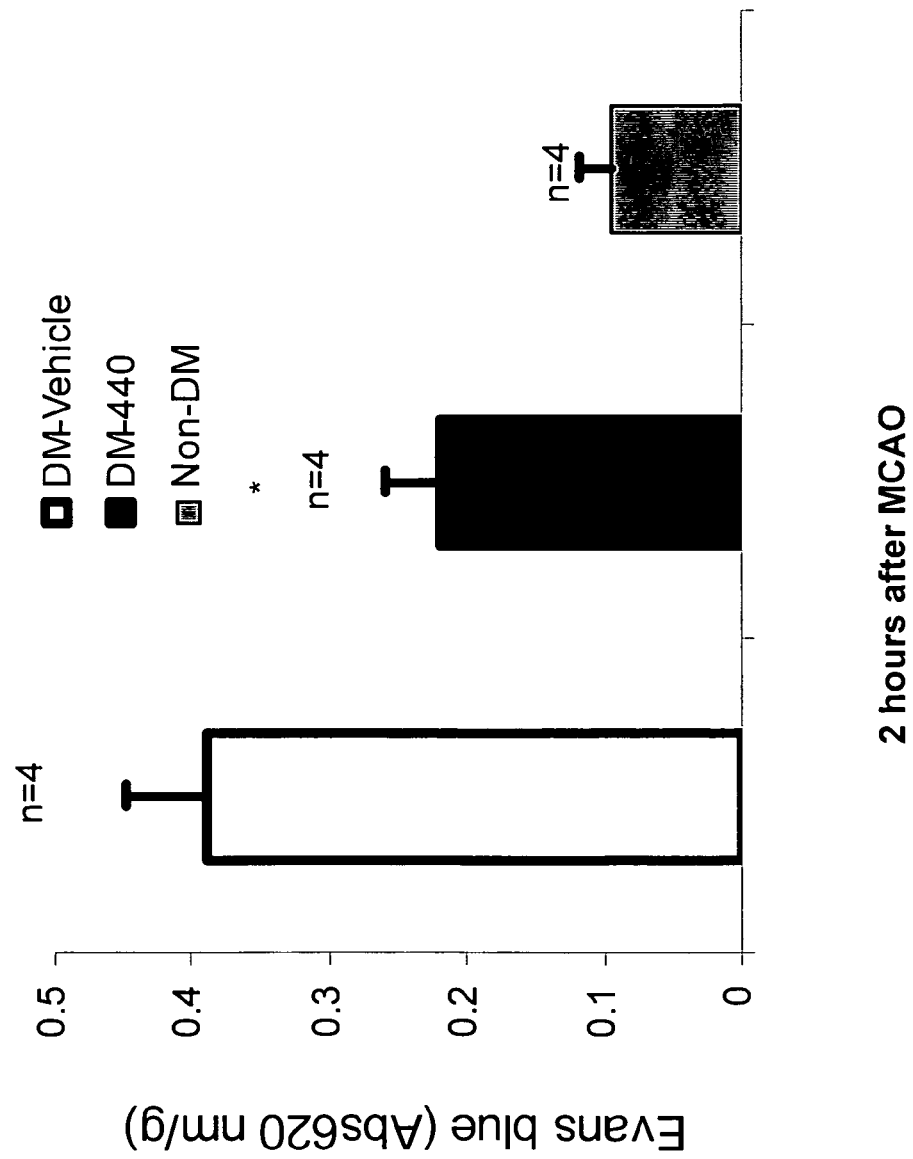
FIG. 14 is a bar graph showing the effect of ASP-440 on cerebral vascular permeability induced by middle cerebral artery occlusion in rats with 4 weeks of STZ-induced diabetes. Rats were implanted with a single subcutaneous osmotic pump containing ASP-440, as indicated. Cerebral vascular permeability was measured using Evan's blue dye method 2 hours after occlusion.
Figure 15:
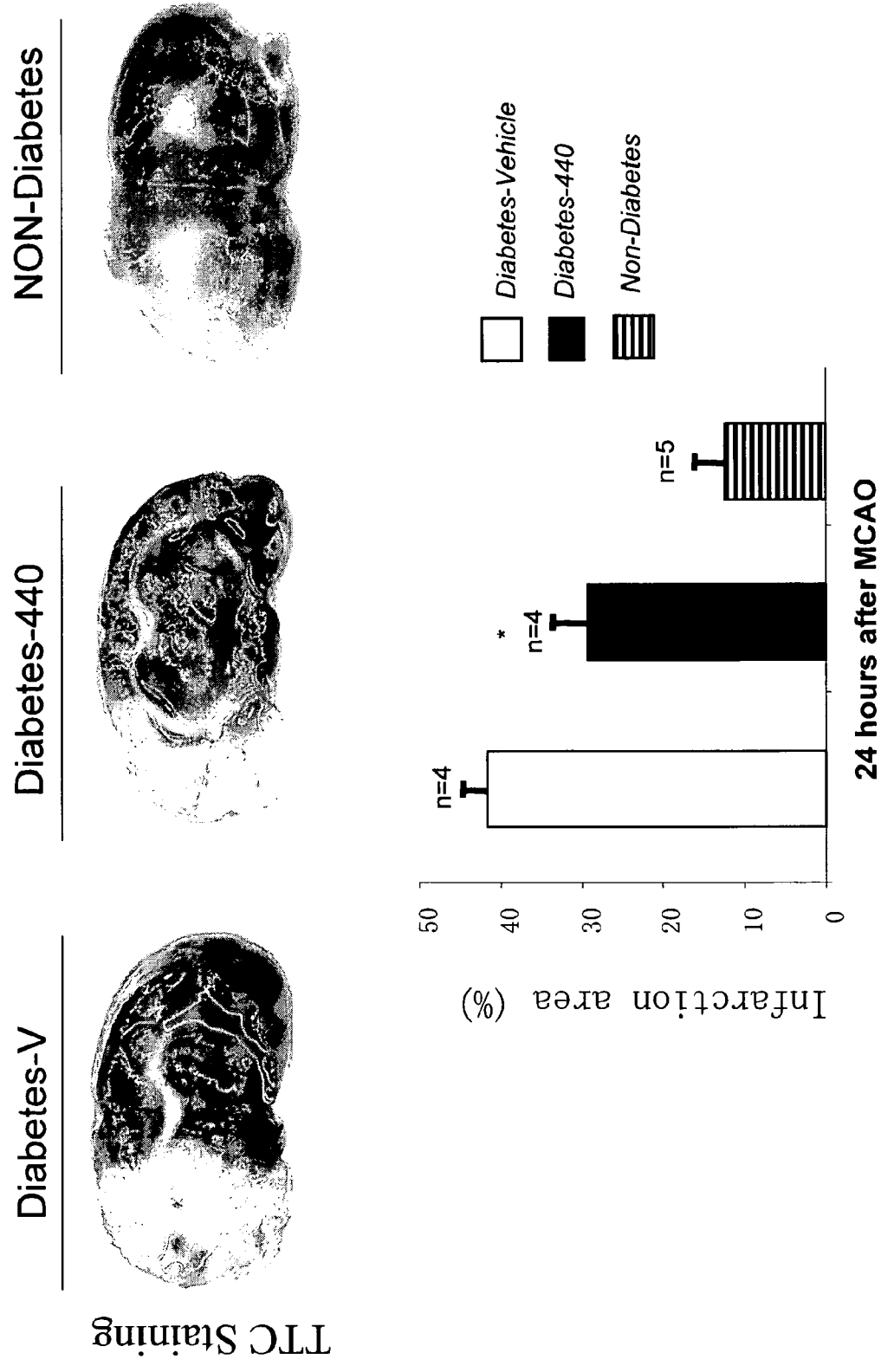
FIG. 15 is a photograph and bar graph showing the effect of ASP-440 on cerebral infarct induced by middle cerebral artery occlusion in rats with 4 weeks of STZ-induced diabetes. Rats were implanted with a single subcutaneous osmotic pump containing ASP-440 (440) or vehicle (V), as indicated. Infarct area was measured using Triphenyltetrazolium chloride stain after 24 hours of permanent occlusion.

Ischemia Increases Cerebral Vascular Permeability by Activated Plasma Kallikrein The effect of diabetes on cerebral vascular permeability induced by ischemia was examined in rats subjected to middle cerebral artery occlusion (MCAO). Rats with 4 weeks of STZ-induced diabetes treated with ASP-440 or vehicle for 3 days and then subjected to MCAO for 2 hrs. Cerebral vascular permeability following MCAO was increased in the diabetic rats compared with nondiabetic rats (FIG. 14). Pretreatment of diabetic rats with ASP-440 via a subcutaneous osmotic pump for 3 days reduced cerebral vascular permeability by about 50% compare with diabetic rats receiving vehicle by osmotic pumps. MCAO-induced infarct area is increased in rats with 4 weeks of diabetes compare with nondiabetic rats (FIG. 15). Treatment of diabetic rats with ASP-440 for 3 days prior to MCAO decreased infarct area by about 40% compared with diabetic rats receiving vehicle (FIG. 15). These data show that plasma kallikrein inhibition by ASP-440 can decrease vascular permeability and cerebral injury induced by ischemia. These results indicate that plasma kallikrein inhibition, as exemplified by ASP-440, can provide protective effects against ischemia-induced vascular permeability and parenchymal injury.

Other Embodiments

All patents, patent applications, and publications mentioned in this specification including U.S. Provisional Application No. 61/063,107, filed Jan. 21, 2008, are herein incorporated by reference to the same extent as if each independent patent, patent application, or publication was specifically and individually indicated to be incorporated by reference.

The invention claimed is:

1. A method for decreasing vascular permeability in a subject in need thereof, said method comprising administering to said subject an effective amount of a compound having the formula I:

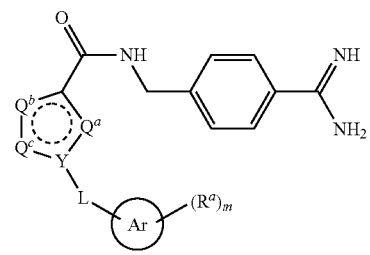

wherein Ar is a bond or an aromatic ring selected from the group consisting of benzene, pyridine, and pyrimidine; the subscript m is an integer of from 0 to 5;
each $R^a$ is independently selected from the group consisting of cycloalkyl, $(C_1-C_8)$haloalkyl, halogen, —OH, —$OR^1$, —$OSi(R^1)_3$, —OC(O)O—$R^1$, —OC(O)$R^1$, —OC(O)$NHR^1$, —OC(O)N$(R^1)_2$, —SH, —$SR^1$, —S(O)$R^1$, —S(O)$_2R^1$, —$SO_2NH_2$, —S(O)$_2NHR^1$, —S(O)$_2N(R^1)_2$, —NHS(O)$_2R^1$, —$NR^1$S(O)$_2R^1$, —C(O)$NH_2$, —C(O)$NHR^1$, —C(O)N$(R^1)_2$, —C(O)$R^1$, —C(O)H, —C(=S)$R^1$, —NHC(O)$R^1$, —$NR^1$C(O)$R^1$, —NHC(O)$NH_2$, —$NR^1$C(O)$NH_2$, —$NR^1$C(O)$NHR^1$, —NHC(O)$NHR^1$, —$NR^1$C(O)N$(R^1)_2$, —NHC(O)N$(R^1)_2$, —$CO_2H$, —$CO_2R^1$, —$NHCO_2R^1$, —$NR^1CO_2R^1$, —$R^1$, —CN, —$NO_2$, —$NH_2$, —$NHR^1$, —N$(R^1)_2$, —$NR^1$S(O)$NH_2$, —$NR^1$S(O)$_2NHR^1$, —$NH_2$C(=$NR^1$)$NH_2$, —N=C($NH_2$)$NH_2$, —C(=$NR^1$)$NH_2$, —NH—OH, —$NR^1$—OH, —$NR^1$—$OR^1$, —N=C=O, —N=C=S, —Si$(R^1)_3$, —NH—$NHR^1$, —NHC(O)$NHNH_2$, NO, —N=C=NR¹, and —S—CN, wherein each R¹ is independently alkyl, aryl, or arylalkyl;

L is a linking group selected from the group consisting of a bond, CH₂, and SO₂; $Q^a$, $Q^b$, and $Q^c$ are each members independently selected from the group consisting of N, S, O, and $C(R^q)$ wherein each $R^q$ is independently selected from the group consisting of H, $C_{1-8}$ alkyl, halo, and phenyl, and the ring having $Q^a$, $Q^b$, $Q^c$, and Y as ring vertices is a five-membered ring having two double bonds;

Y is a member selected from the group consisting of C and N;

when Ar is a bond, m is 1;

when Ar is an aromatic ring, m is an integer of from 0-5; and pharmaceutically acceptable salts thereof.

2. The method of claim 1, wherein Ar is an aromatic ring selected from the group consisting of benzene, pyridine, and pyrimidine.

3. The method of claim 1, wherein Ar is a bond and m is 1.

4. The method of claim 1, wherein said compound has the formula Ia:

Ia

5. The method of claim 2, wherein L is a bond and Y is N.

6. The method of claim 2, wherein L is a bond, Y is N and Ar is a benzene ring.

7. The method of claim 6, wherein $Q^a$, $Q^b$, and $Q^c$ are each independently $C(R^q)$.

8. The method of claim 6, wherein $Q^b$ is N.

9. The method of claim 2, wherein Y is C; $Q^a$ is S, and Ar is selected from the group consisting of phenyl and pyridyl.

10. The method of claim 9, wherein $Q^c$ is C.

11. The method of claim 2 wherein L is CH₂ and Y is N.

12. The method of claim 11, wherein $Q^a$ is C.

13. The method of claim 12, wherein $Q^b$ and $Q^c$ are each independently selected from the group consisting of N and $C(R^q)$.

14. The method of claim 12, wherein Ar is benzene or pyridine.

15. The method of claim 2, wherein L is a bond and Y is C.

16. The method of claim 15, wherein $Q^b$ is O; and $Q^a$ and $Q^c$ are each $C(R^q)$.

17. The method of claim 2, wherein L is SO₂ and Y is N.

18. The method of claim 2, wherein each $R^a$ is independently selected from the group consisting of $C_1$-$C_8$ alkyl, $C_1$-$C_8$ alkoxy, aryl, aryl($C_1$-$C_8$ alkyl), halogen, —NH₂, —NH($C_1$-$C_8$ alkyl), —N($C_1$-$C_8$ alkyl)₂, —CN, —C(=O)($C_1$-$C_8$ alkyl), —(C=O)NH₂, —(C=O)NH($C_1$-$C_8$ alkyl), —C(=O)N($C_1$-$C_8$ alkyl)₂, —OH, —COOH, —COO($C_1$-$C_8$ alkyl), —OCO($C_1$-$C_8$ alkyl), —O(C=O)O($C_1$-$C_8$ alkyl)-NO₂, —SH, —S($C_1$-$C_8$ alkyl), —NH(C=O)($C_1$-$C_8$ alkyl), —NH(C=O)O($C_1$-$C_8$ alkyl), —O(C=O)NH($C_1$-$C_8$ alkyl), —SO₂($C_1$-$C_8$ alkyl), —NHSO₂($C_1$-$C_8$ alkyl), and —SO₂NH($C_1$-$C_8$ alkyl).

19. The method of claim 18, wherein each $R^a$ is independently selected from the group consisting of $C_1$-$C_8$ alkyl, $C_1$-$C_8$ alkoxy, phenyl, phenyl ($C_1$-$C_8$ alkyl), halogen, —CN, —NH₂, —NH($C_1$-$C_8$ alkyl), —N($C_1$-$C_8$ alkyl)₂, —(C=O)CH₃, —(C=O)NH₂, —OH, —COOH, —COO($C_1$-$C_8$ alkyl), —OCO($C_1$-$C_8$ alkyl), —O(C=O)O($C_1$-$C_8$ alkyl), —NO₂, —SH, —S($C_1$-$C_8$ alkyl), and —NH(C=O)($C_1$-$C_8$ alkyl).

20. The method of claim 19, wherein $R^a$ is halogen.

21. The method of claim 2, wherein said compound is selected from the group consisting of:

37
-continued

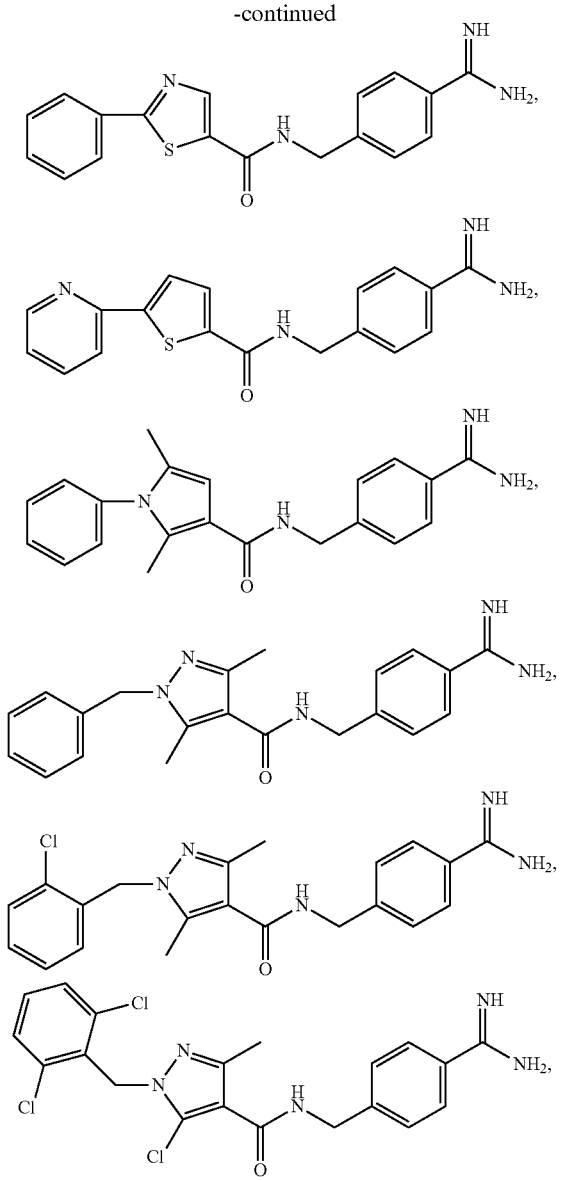

38
-continued

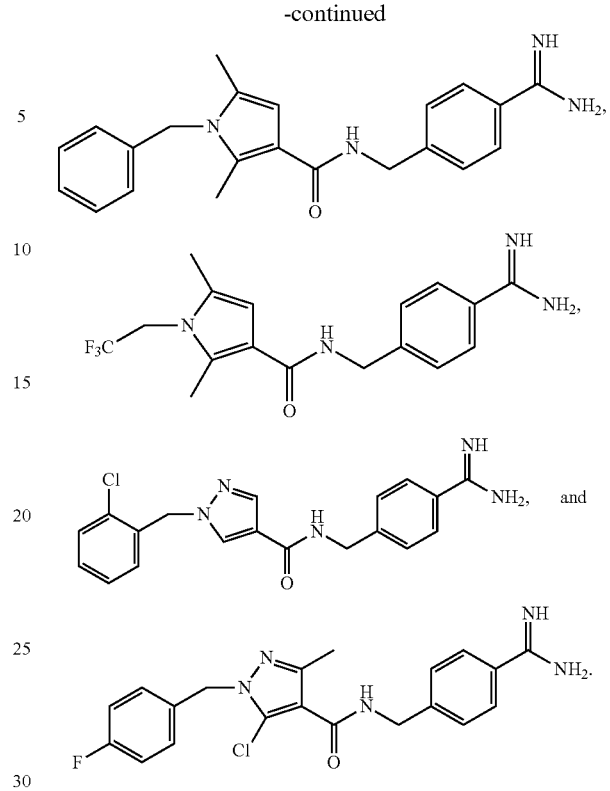

22. The method of claim 1, wherein said subject has increased vascular permeability.

23. The method of claim 1, wherein said subject has type 1 or type 2 diabetes, hypertension, insulin resistance, ketoacidosis, trauma, infection, or hyperglycemia.

24. The method of claim 1, wherein said subject has suffered from, or is at increased risk of having, a hemorrhagic stroke, an intracerebral hemorrhage, a hemorrhagic transformation of ischemic stroke, a cerebral trauma associated with injury or surgery, a brain aneurysm, a high altitude edema, or arterial-venous malformation.

\* \* \* \* \*